United States Patent [19]
Bartfeld et al.

[11] Patent Number: 5,360,729
[45] Date of Patent: Nov. 1, 1994

[54] METHOD FOR PURIFICATION OF RECOMBINANT COPPER/ZINC (CU-ZN) SUPEROXIDE DISMUTASE FROM BACTERIA OR EUCARYOTIC CELLS

[75] Inventors: Daniel Bartfeld, North York, Canada; Ruth Lieshitz, Rehovot, Israel; Dany Hadary, Richmond Hill, Canada

[73] Assignee: Bio-Technology General Corp., New York, N.Y.

[21] Appl. No.: 29,030

[22] Filed: Mar. 10, 1993

Related U.S. Application Data

[63] Continuation of Ser. No. 840,571, Feb. 24, 1992, abandoned, which is a continuation of Ser. No. 432,871, Nov. 7, 1989, abandoned.

[51] Int. Cl.$^5$ .............................................. C12N 9/02
[52] U.S. Cl. .................................. 435/189; 435/815; 435/816
[58] Field of Search ............................. 435/189, 815

[56] References Cited

U.S. PATENT DOCUMENTS 4,742,004  5/1988  Hartman et al. ..................... 435/70

FOREIGN PATENT DOCUMENTS 252615  12/1987  Germany .
7150782  9/1982  Japan .
3049078  3/1988  Japan .
9005181  5/1990  WIPO .

OTHER PUBLICATIONS

Weng, Q. et al. (1989) Chem. Abst. 110:53519v.
Grunow, M., et al. (1988) Chem. Abst. 109:225811j.
Fridovich, I. (1986) Enzymology 58, 61–97.
Ksjihara, J. I., et al. (1988) J. Biochem 104, 638–642.

*Primary Examiner*—Charles L. Patterson, Jr.
*Attorney, Agent, or Firm*—John P. White

[57] ABSTRACT

The subject invention provides a method for recovering a solution containing purified, enzymatically active Cu-Zn superoxide dismutase or a polypeptide analog thereof having substantially the same amino acid sequence as, and the bioloical activity of, naturally-occurring Cu-Zn superoxide dismutase from a composition which comprises cells containing Cu-Zn superoxide dismutase or a polypeptide analog thereof. The invention also provides a method of increasing the yield of recovered solutions having an increased concentration of b isoform of an enzymatically-active polypeptide analog of Cu-Zn superoxide dismutase from a composition which comprises cells containing a, b and c isoforms of the polypeptide analog.

17 Claims, 19 Drawing Sheets

METHOD FOR PURIFICATION OF RECOMBINANT COPPER/ZINC (CU-ZN) SUPEROXIDE DISMUTASE FROM BACTERIA OR EUCARYOTIC CELLS

This application is a continuation of U.S. Ser. No. 840,571, filed Feb. 24, 1992, now abandoned which is a continuation of U.S. Ser. No. 432,871, filed Nov. 7, 1989, now abandoned.

BACKGROUND OF THE INVENTION

Throughout this application, various publications are referenced by Arabic numerals within parentheses. Full citations for these references may be found at the end of the specification immediately preceding the claims. The disclosures of these publications in their entireties are hereby incorporated by reference in this application in order to more fully describe the state of the art to which this invention pertains.

This invention provides an improved method for purification of recombinant copper/zinc (Cu-Zn) superoxide dismutase from bacteria or eucaryotic cells.

The clinical potential of the enzyme superoxide dismutase (SOD) is enormous. The scientific literature suggests that SOD could be useful in a wide range of clinical applications. These include prevention of oncogenesis and tumor growth and reduction of cytotoxic and cardiotoxic effects of anticancer drugs, anti-inflammatory protection of ischemic tissues and protection of spermatozoa. In addition, there is great interest in studying the effect of SOD on the aging process. There is also evidence that SOD can be used to prevent the damage sometimes caused to newborn babies by hyperbaric oxygen treatment.

In particular, there is increasing evidence that "reperfusion injury" caused by oxygen free radicals (probably generated from xanthine oxidase) accounts for much of the damage caused by a period of ischemia in many organs of the body such as the spinal cord, intestine, skin, heart, lung, pancreas or kidney (11).

In vitro and animal experiments using human recombinant copper/zinc superoxide dismutase (hCu-Zn SOD analog), produced as described in coassigned U.S. Pat. No. 4,742,004, issued May 2, 1988, and in corresponding European patent application publication no. 0173280, published May 5, 1986, have demonstrated the efficacy of SOD in reducing reperfusion injury e.g., in the spinal cord of dogs (12), in the hearts of rabbits (13), and in the hearts of dogs (14).

The superoxide anion ($0°_2$) produced on reperfusion of ischemic tissue and also in certain inflammatory conditions is highly toxic to macromolecules, e.g., $0°_2$ may react with lipid hydroperoxides to form alkoxy radicals in phospholipid membranes.

The superoxide anion ($0°_2$) is removed in normal biologic tissue by the dismutation reaction:

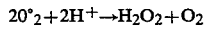

$$2 0°_2 + 2H^+ \rightarrow H_2O_2 + O_2$$

The above reaction can proceed spontaneously or it can be catalyzed by SOD which increases the rate of intercellular dismutation by a factor of $10^9$. SOD is a ubiquitous mammalian enzyme. In the presence of normal intercellular concentrations of catalase and peroxidase, SOD is responsible for the "scavenging" of oxygen-free radicals, thereby serving as a normal biological defense against the formation and accumulation of reduced oxygen intermediates.

Copper/zinc (Cu-Zn) SOD has been demonstrated in virtually all eucaryotic organisms. Human Cu-Zn SOD-1 is a dimeric metallo-protein composed of identical non-covalently linked subunits, each having a molecular weight of 16,000 daltons and containing one atom of copper and one of zinc. Each subunit is composed of 153 amino acids whose sequence has been established.

Endogenous SOD is present in tissues in limited amounts and when high levels of superoxide anion are produced, the amount of SOD present is not sufficient. Thus there is a need for clinical administration of exogenous SOD. However, exploration of the therapeutic potential of human SOD-1 (EC 1.15.1.1) has been limited mainly due to its scarce availability. To overcome this problem we inserted an SOD clone containing the entire coding region of human SOD-1 described by Groner and his colleagues (15) into efficient bacterial expression vectors which express hSOD analog at high levels; this has been described in coassigned U.S. Pat. No. 4,742,004 described above. Using this method, we have produced recombinant hSOD analog which differs from authentic human SOD (from blood) in that the amino terminus alanine is not acetylated. The amino acid sequence of the bacterial-produced SOD analog does not contain a methionine residue at its N-terminus.

The recombinant hSOD analog thus produced is very pure. However, it was desirable to produce even higher levels of purity. An improved chromatography method which produces an even higher degree of purification, surprisingly achieved without loss of yield, is described in this application. A novel "exchange" procedure which increases the yield of pure recombinant SOD produced, without loss of purity, is also described.

European patent application publication no. 0180964, published May 14, 1986 and assigned to Ube Industries Limited, discloses the production of human Cu-Zn SOD in *Escherichia coli* and partial purification of the hSOD produced. This method was done on small scale only (20 g of wet cells). No details of purification achieved are given apart from specific activity. There is no disclosure of the extent of contamination by *Escherichia coli* proteins and endotoxins.

European patent application publication no. 0138111, published Apr. 24, 1985 and assigned to Chiron Corporation, discloses the production of hSOD in both *Escherichia coli* and yeast, but no methods of production of hSOD from crude cell lysates are disclosed. European patent application publication no. 0164556, also assigned to Chiron, discloses the production of a yeast expression plasmid for hSOD, but again no methods of purification of hSOD are disclosed.

Hallewell et al. from Chiron Corporation (16) disclose production of recombinant SOD but merely state that the recombinant SOD was purified to homogeneity by conventional means after lysing the yeast cells with glass beads and pelleting the cell debris.

Hallewell et al. from Chiron Corporation (17) disclose a method of purifying recombinant SOD from yeast cells. This method gives no detail of the yield of hSOD produced, nor its degree of purification; it is also a purification method of hSOD analog from yeast cells and not *Escherichia coli* cells.

Takahara et al. (18) disclose the secretion by *Escherichia coli* cells of hSOD into the periplasmic space. This is a very small-scale procedure (16 ml medium), and the SOD produced is not purified; the *Escherichia coli* cells are simply subjected to osmotic shock, and subcellular fractions are analyzed by SDS-PAGE.

SUMMARY OF THE INVENTION

The subject invention provides a method for recovering a solution containing purified, enzymatically active Cu-Zn superoxide dismutase or a polypeptide analog thereof having substantially the same amino acid sequence as, and the biological activity of, naturally-occuring Cu-Zn superoxide dismutase from a composition which comprises cells containing Cu-Zn superoxide dismutase or a polypeptide analog thereof comprising:

(a) treating the composition so as to separate soluble proteins present in the cells from whole cells, cellular debris and insoluble proteins so as to obtain a solution containing such soluble proteins;

(b) treating the resulting solution containing the soluble proteins with a second solution containing a salt at a concentration such that the soluble proteins other than Cu-Zn superoxide dismutase or the polypeptide analog thereof present in the solution containing the soluble proteins are rendered capable of binding to an appropriate hydrophobic substance;

(c) contacting the then-resulting solution containing the soluble proteins with an appropriate hydrophobic substance so as to bind the soluble proteins other than Cu-Zn superoxide dismutase or the polypeptide analog thereof present in such solution to the hydrophobic substance and thus separate such other proteins from the Cu-Zn superoxide dismutase or polypeptide analog thereof; and (d) recovering the resulting solution containing purified, enzymatically active Cu-Zn superoxide dismutase or polypeptide analog thereof.

Also provided is a method of increasing the yield of recovered solutions having an increased concentration of b isoform of an enzymatically-active polypeptide analog of Cu-Zn superoxide dismutase from a composition which comprises cells containing a, b and c isoforms of the polypeptide analog which comprises:

(a) treating the composition so as to separate soluble proteins present in the cells from whole cells, cellular debris and insoluble proteins so as to obtain a solution containing such soluble proteins, including the a, b and c isoforms;

(b) treating the resulting solution containing the soluble proteins so as to produce three separate solutions, each of which has an increased concentration of one of either of the a, b or c isoform;

(c) recovering the separate solution which has an increased concentration of the b isoform;

(d) combining the separate solution which has an increased concentration of the a isoform with the separate solution which has an increased concentration of the c isoform;

(e) treating the resulting combined solution so as to produce a solution which has an increased concentration of the b isoform; and (f) recovering the then-resulting solution which has an increased concentration of the b isoform.

Figure 1:
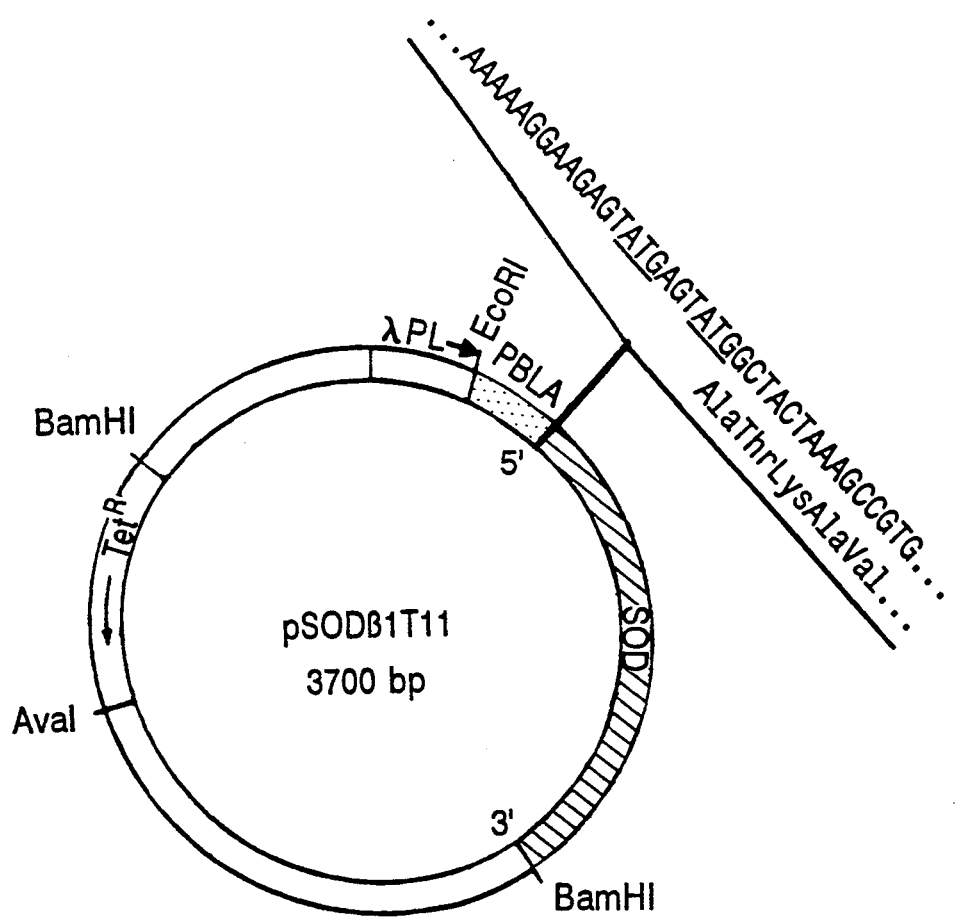
FIG. 1. Plasmid pSOD$\beta_1$T11-a high level expressor of Cu-Zn SOD analog protein The construction of plasmid pSOD$\beta_1$T11 has been fully described in co-assigned, copending European patent application publication no. 0173280, published on May 5, 1986 (corresponding to U.S. patent application Ser. No. 644,105, filed Aug. 27, 1984, issued May 2, 1988 as U.S. Pat. No. 4,742,004), and pSOD$\beta_1$T11 has been deposited in the ATCC under Accession No. 53468. This plasmid contains the following elements.

(a) the origin of replication of plasmid pBR322;

(b) the Tet$_r$ gene of plasmid pBR322 in counterclockwise orientation; and (c) in clockwise orientation and in 5' to 3' order the $\lambda$ P$_L$O$_L$ promoter/operator region, the $\beta$-lactamase promoter and ribosomal binding site, and the coding sequence for hSOD analog.

Plasmid pSOD $\beta_1$T11 is a high level expressor of hSOD analog protein under the control of the strong leftward promoter of bacteriophage $\lambda$ (P$_L$) which is thermoinducibly controlled by the cI857 temperature sensitive repressor situated on the host chromosome.

FIG. 2. Preparative ion exchange chromatography of hSOD analog solution

A. DEAE-Sepharose FF column (15×37 cm)

This column may be used in the ion-exchange chromatography step of the method for purifying hSOD analogs. Application of hSOD analog solution to the DEAE-Sepharose FF column and elution conditions on the column are as described in the text (Example 3E).

DW1, DW2, DW3, DW4=eluate from washing step (20 mM tris-25 mM NaCl at pH=7.8)

First arrow=step change in eluent to 20 mM tris-80 mM NaCl at pH=7.8

DMP (hatched peak)=main hSOD analog peak (collected and saved)

Second arrow=addition of high salt solution for regeneration of the column

The black peaks (DW4 and DE1) can be collected and treated as described in Example 4B.

B. CM-Sepharose FF column (15×37 cm)

The CM-Sepharose FF column may also be used in the ion-exchange chromatography step of the method for purifying hSOD analog. Application of the hSOD analog solution to the CM-Sepharose FF columns and solution conditions on the column are as described in the text (Example 3F).

CW1, CW2=eluate from washing steps (40 mM sodium acetate pH 4.8)

First arrow=step change in eluent to 85 mM sodium acetate pH 4.8

CMP (black peak)=main hSOD analog peak which is collected and saved

Second arrow=addition of high salt solution (0.5M NaCl)

The black peaks CW2, CE1 and CE2 can be collected and treated as described in Example 4B.

FIG. 3. Analytical fast performance anion exchange chromatography on Mono Q (HR 5/5) column of isolated isoforms of hSOD analog and mixtures thereof A: isolated isoform a of hSOD analog (2.5 mg/ml).

B: isolated isoform c of HSOD analog (2.5 mg/ml).

C: mixture (1:1) of isolated isoforms a (5 mg/ml) and c (5 mg/ml) without incubation.

D, E and F: the same mixture of isolated isoforms a and c as shown in panel C but incubated at 37° C. for 30, 60 and 240 minutes respectively.

The samples were dissolved in buffer A (25 mM bis-Tris-HCl, pH 7.0) and 100 $\mu$l of the solution was injected onto an analytical fast performance Mono Q (HR 5/5) column. The elution was performed with gradient of 100% buffer A to 100% buffer B (same as buffer A but containing 0.25M NaCl); flow rate 1.5 ml/min; chart speed 1.0 cm/min; detection at 280 nm and 0.2 AUFS (AUFS=absorbance ultraviolet full scale).

Figure 3A:
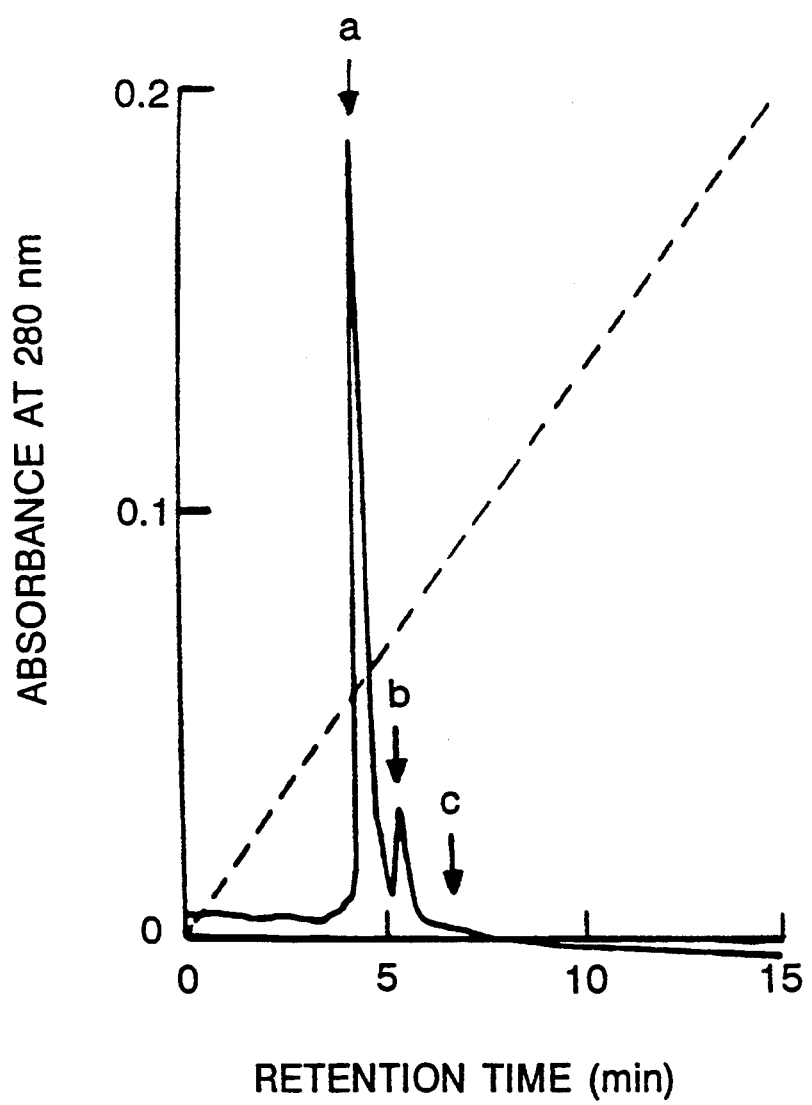
Figure 3B:
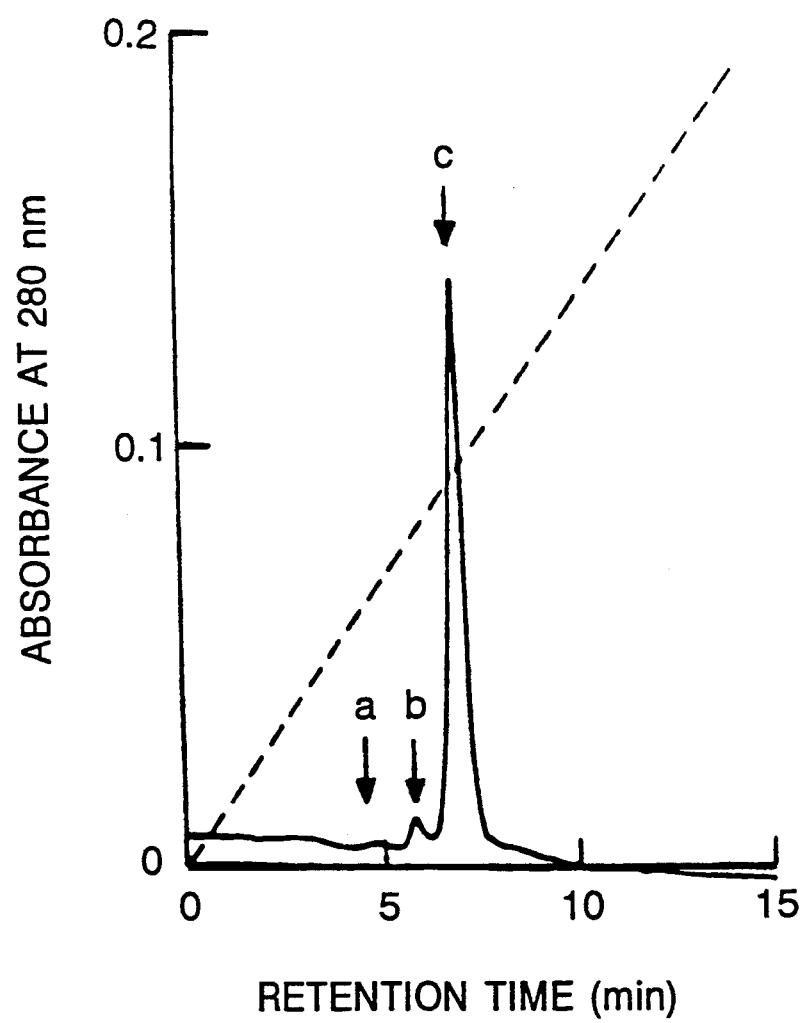
Figure 3C:
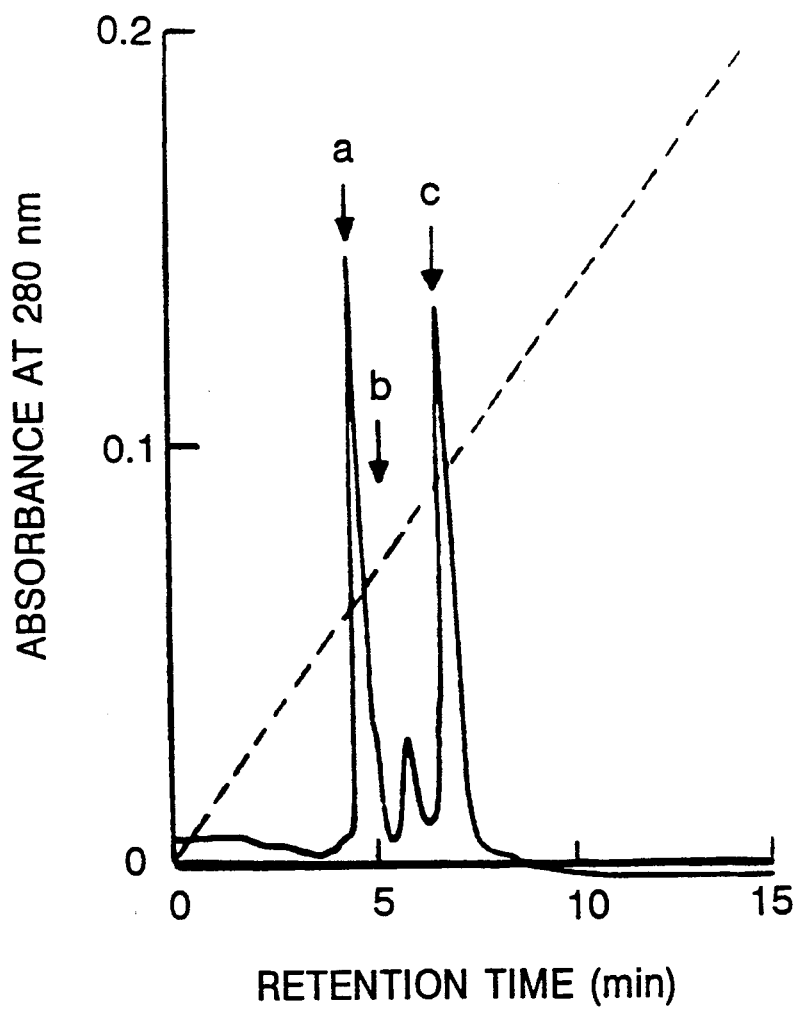
Figure 3D:
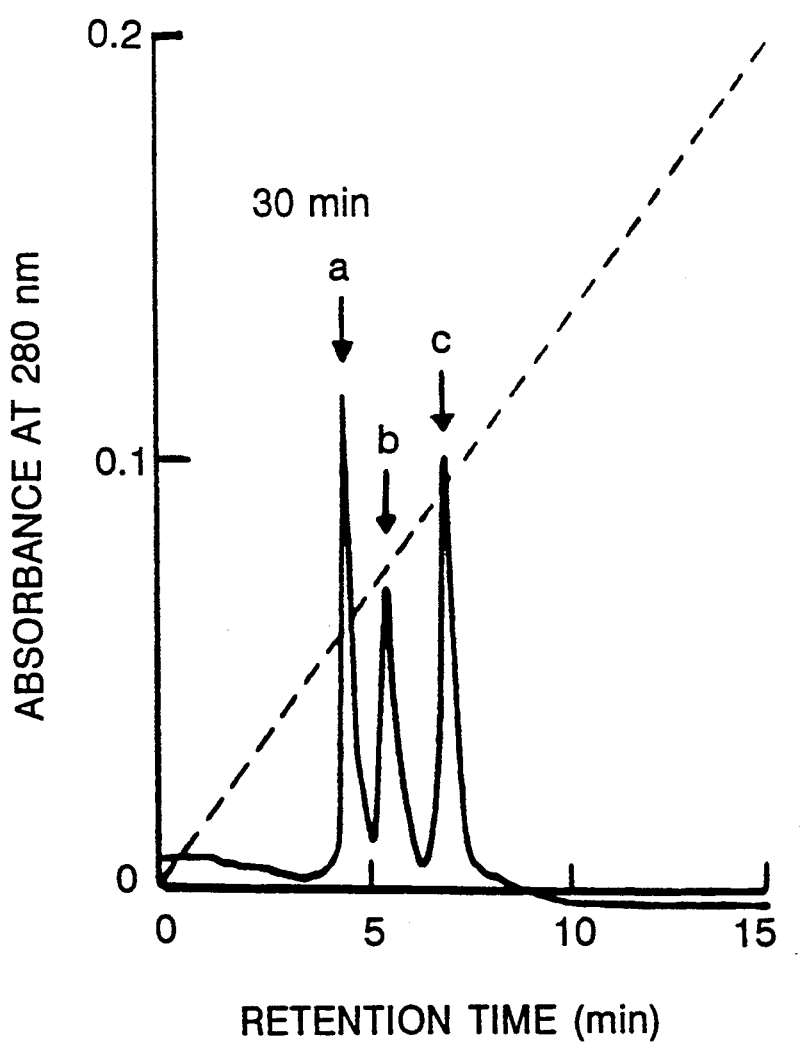
Figure 3E:
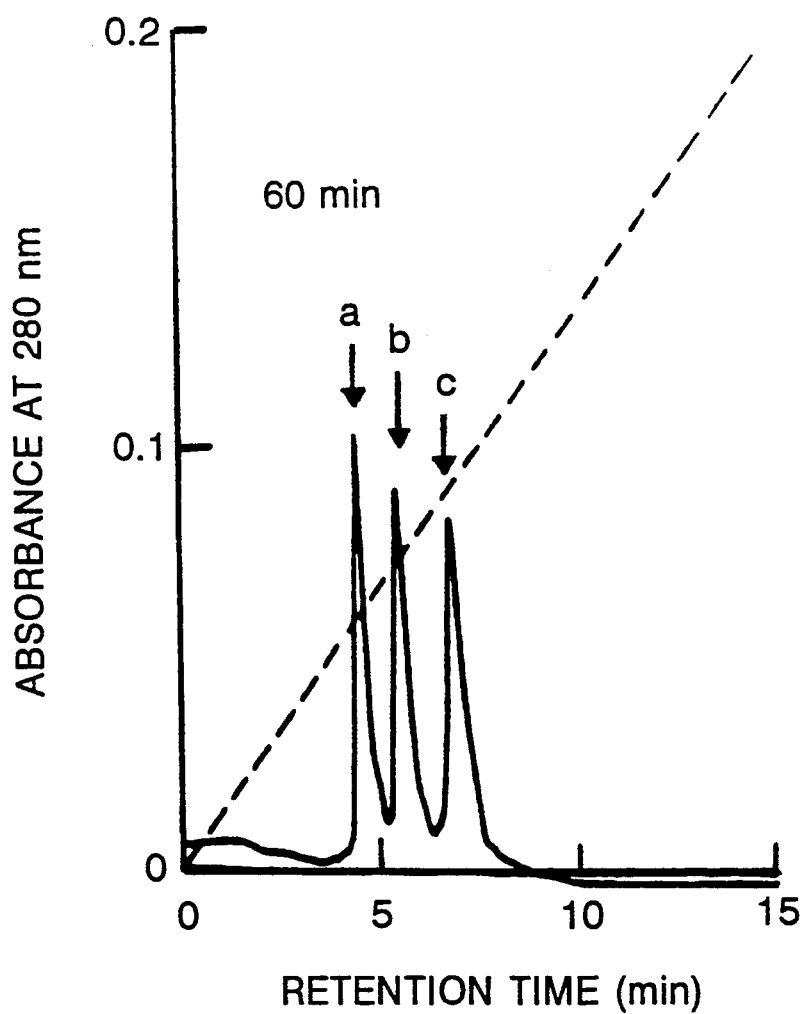
Figure 3F:
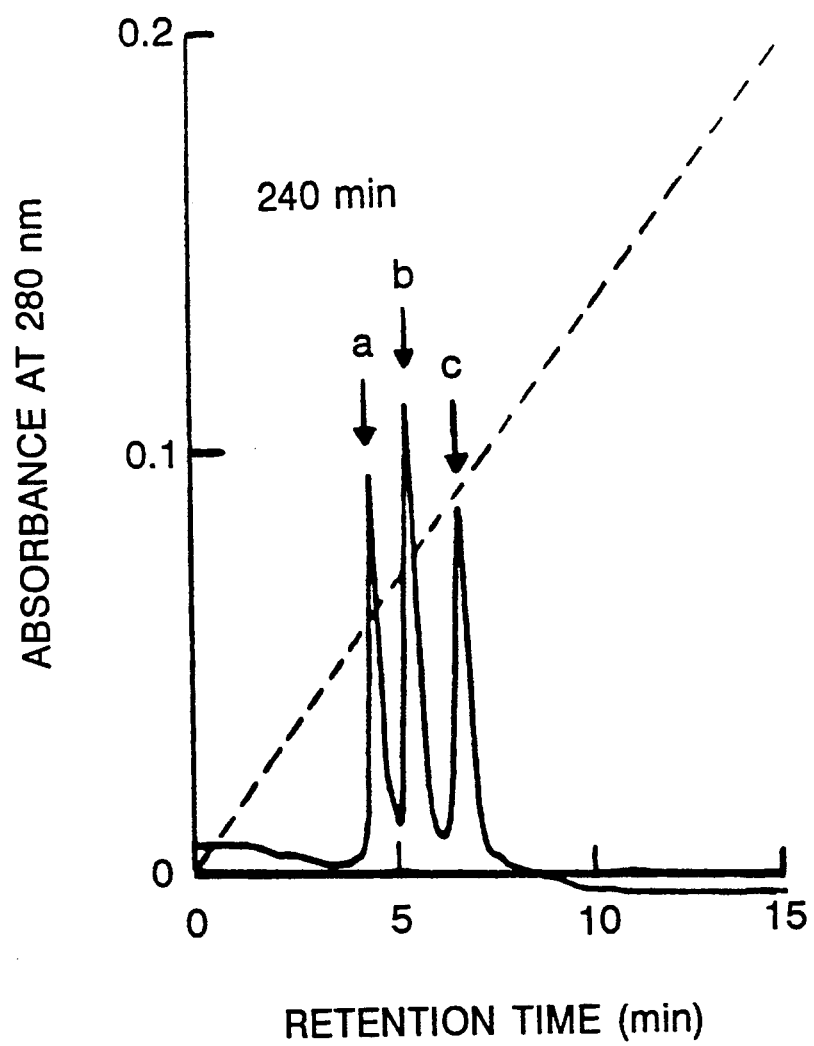
Figure 4:
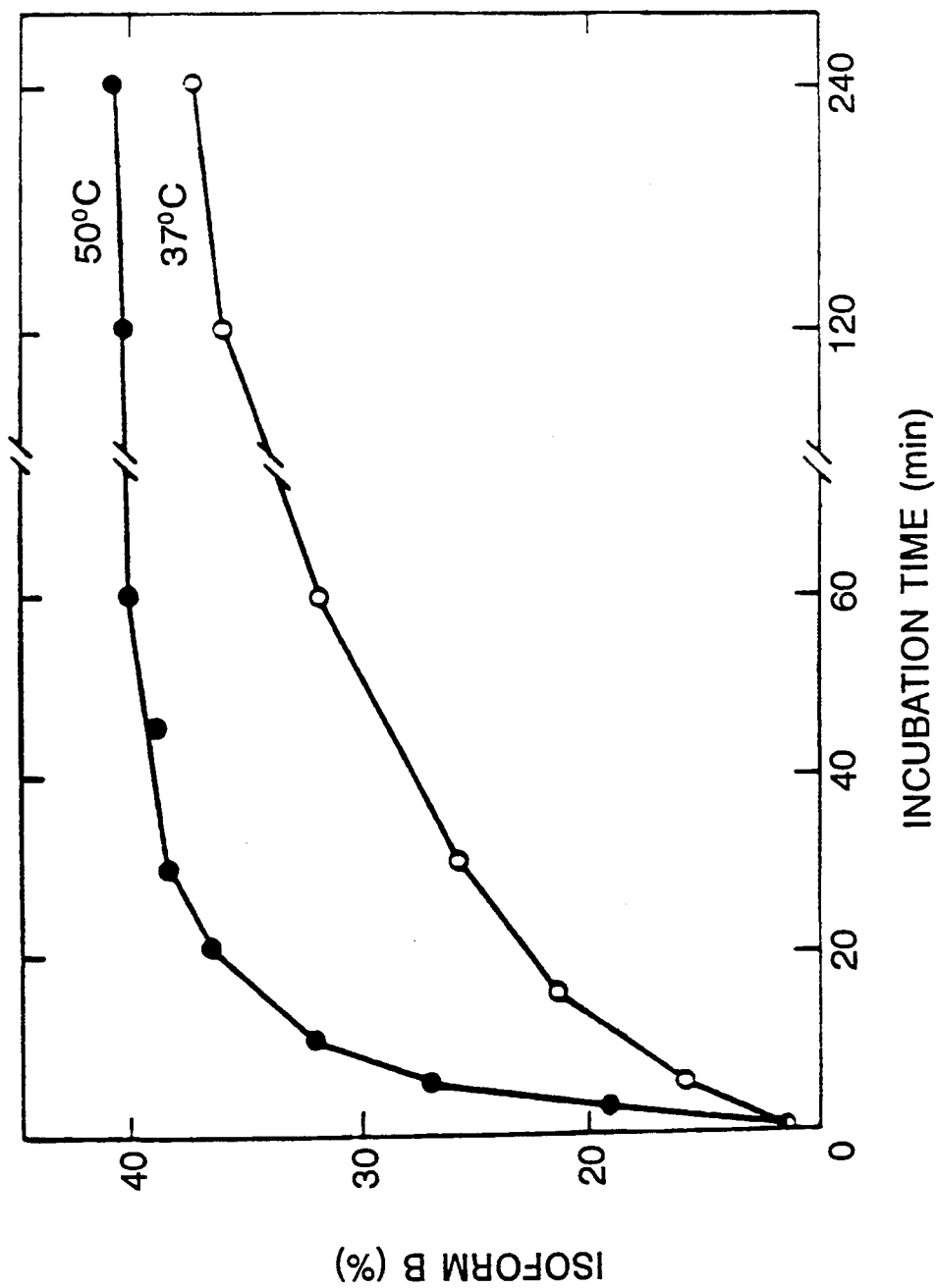

FIG. 4. Time course of production of isoform b on incubation of a mixture of isolated isoforms a and c A mixture of isolated isoforms a and c as described in FIG. 3C was incubated at 37° C. for various time intervals from 0–240 minutes. The analysis on an analytical Mono Q (HR 5/5) column was described in FIG. 3.

o=incubation at 37° C.

● =incubation at 50° C.

Figure 5A:
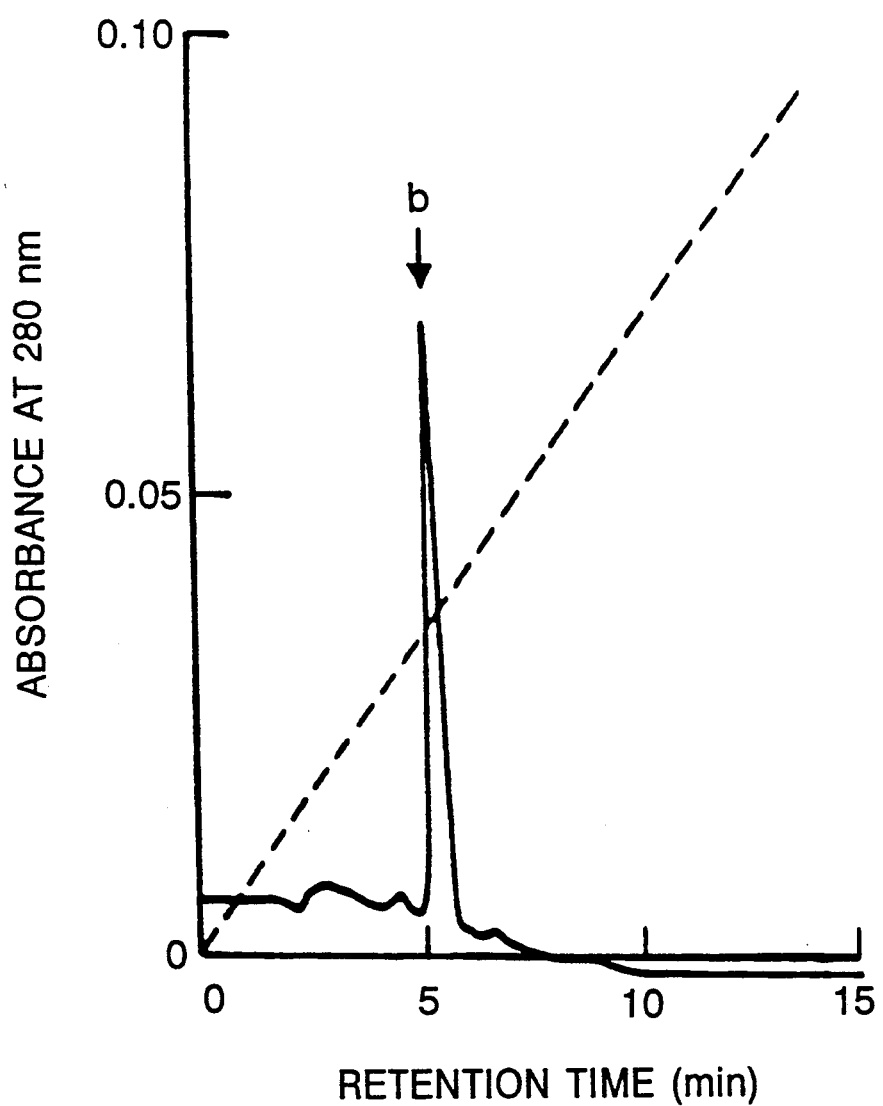
Figure 5B:
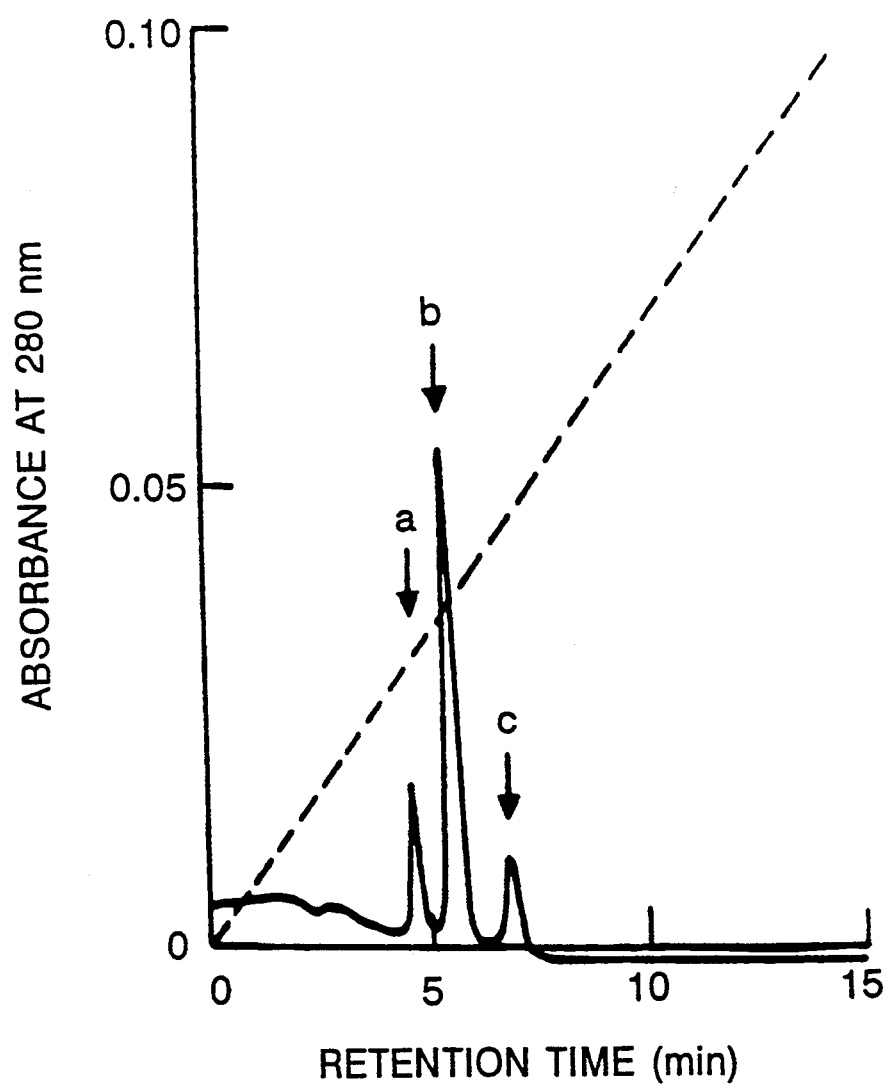
Figure 5C:
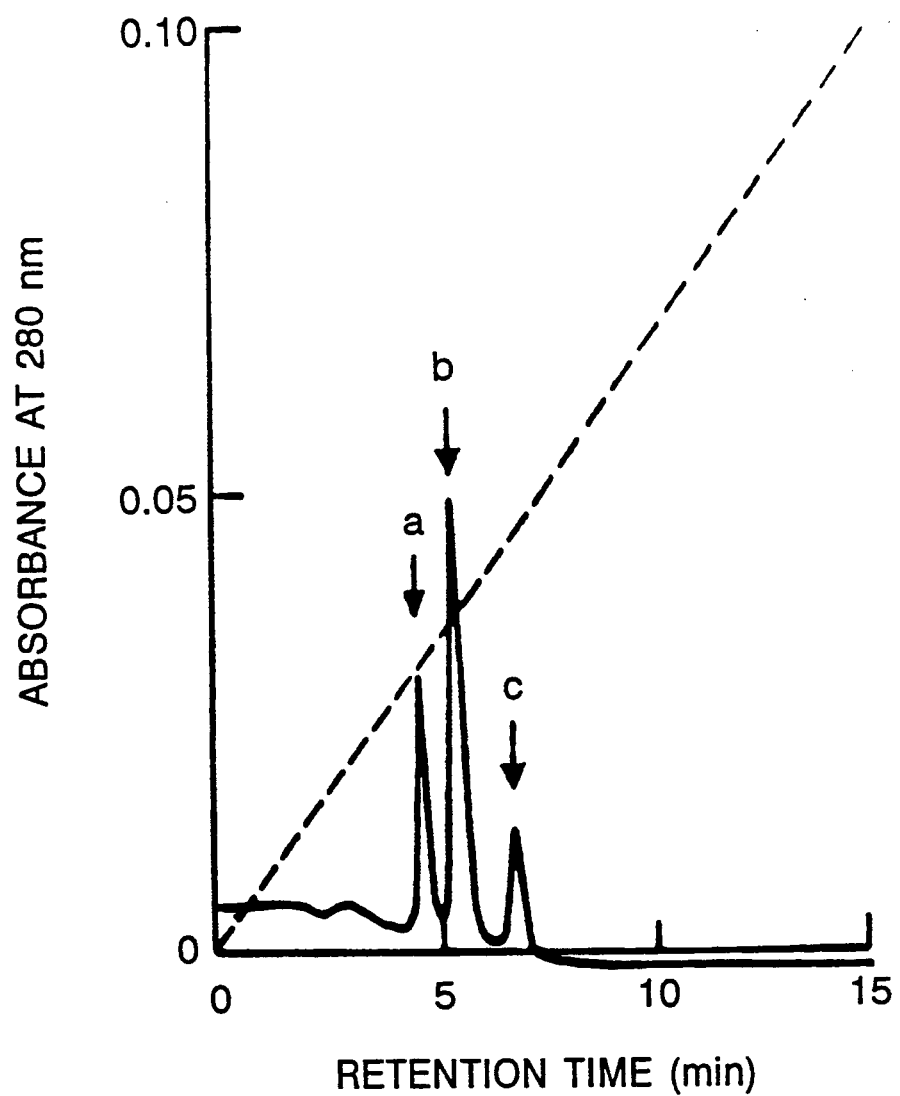

FIG. 5. Analytical fast performance anion exchange chromatography on Mono Q (HR 5/5) column of isolated Mono Q resolved isoform b of hSOD analog protein Isoform b was preparatively isolated from a mixture of isolated isoforms a and c, following incubation for 24 hours at 37° C., by preparative fast performance chromatography on Mono Q (HR 10/10) column. The isoform b peak eluted was collected and immediately frozen at −20° C. The samples were defrosted and diluted 1:3 with $H_2O$ (yielding approximately 0.45 mg/ml). 200 μl of the solution was injected onto an analytical fast performance anion exchange Mono Q (HR 5/5) column. The elution was performed as described in FIG. 3, except the detection at 280 nm was 0.05 AUFS.

A: isoform b injected immediately after defrosting.

B: isoform b incubated at 37° C. for one hour.

C: isoform b incubated at 37° C. for 24 hours.

Figure 6A:
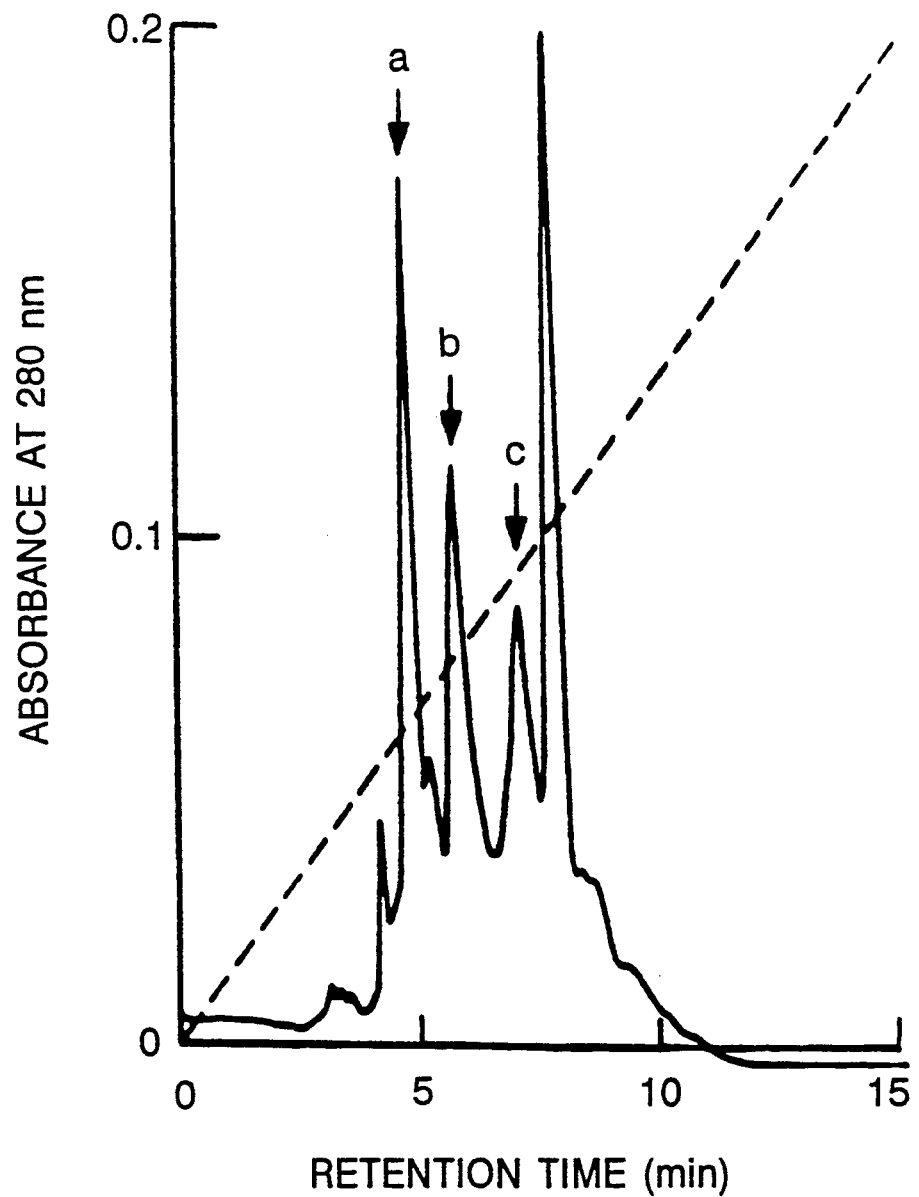
Figure 6B:
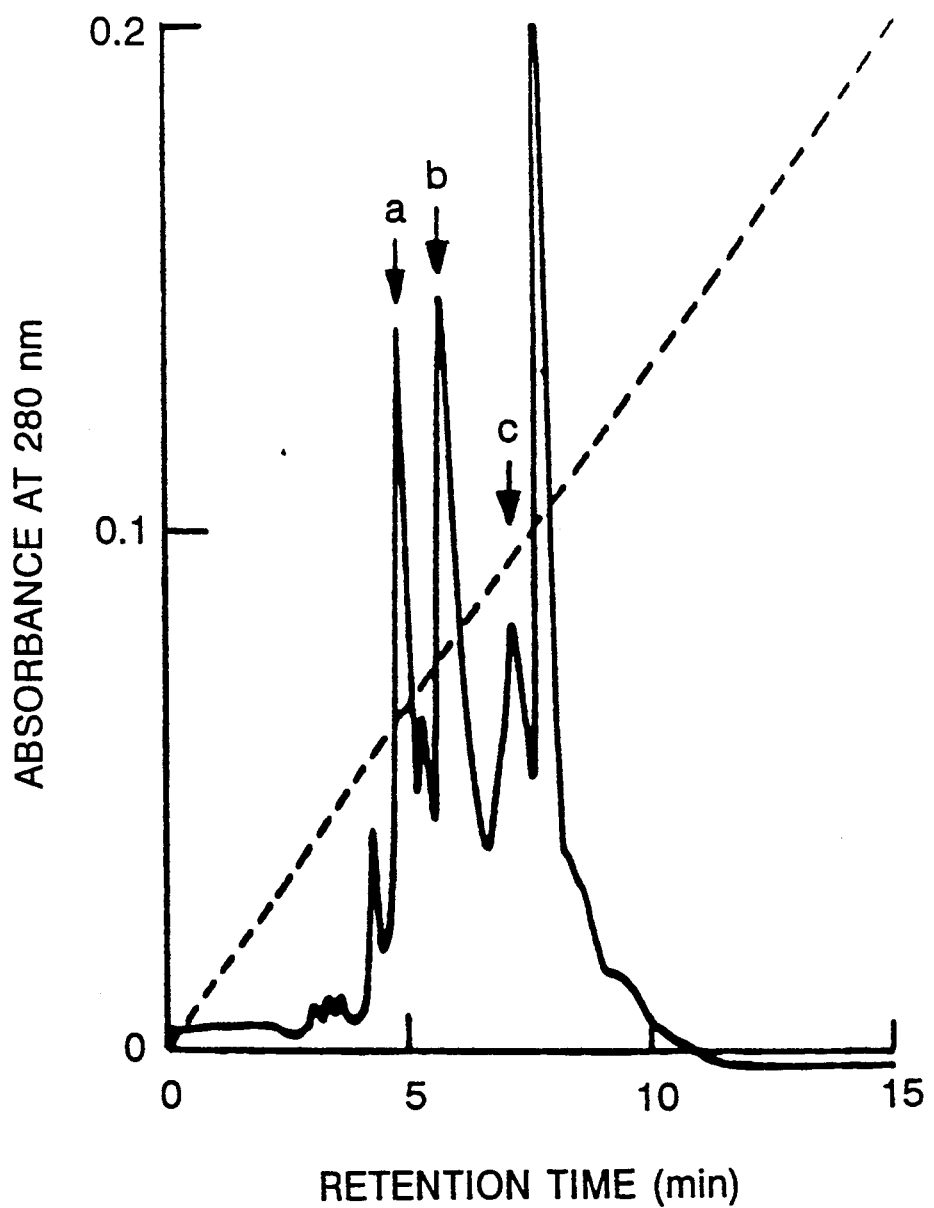

FIG. 6. Analytical fast performance anion exchange chromatography on Mono Q (HR 5/5) column of a sample from the mixture of the DW4, DE1, CW2, CE1 and CE2 fractions (FIG. 2) derived from DEAE-Sepharose I and CM Sepharose I (steps E and F in scheme I) in the process preparation of hSOD analog A: the mixture was injected immediately after the relative fraction mixing.

B: the mixture was injected after incubation for two hours at 37° C. and 20 hours at room temperature.

In both cases 50 μl (approximately 11 mg/ml) of sample was injected. The elution was performed as described in FIG. 3.

FIG. 7. Preparative ion-exchange chromatography of the hSOD analog preparation produced by the exchange procedure The mixture of the DW4, DE1, CW2, CE1 and CE2 hSOD analog fractions derived from Example 3 steps E and F (the black peaks in FIG. 2) were treated as described in Example 4 (exchange procedure including dialysis and incubation steps).

A: after the incubation step of the exchange procedure, 4 ml of mixture was applied to the DEAE Sepharose column. Application and elution conditions were the same as FIG. 2.

The peak shaded black (DMP fraction) was collected and dialyzed against 40 mM sodium acetate pH 4.8.

B: the sample after dialysis was applied to a CM Sepharose column. Application and elution conditions are the same as FIG. 2.

The peak shaded black (CMP) containing hSOD analog is collected, saved and added to the bulk preparation.

Figure 7A:
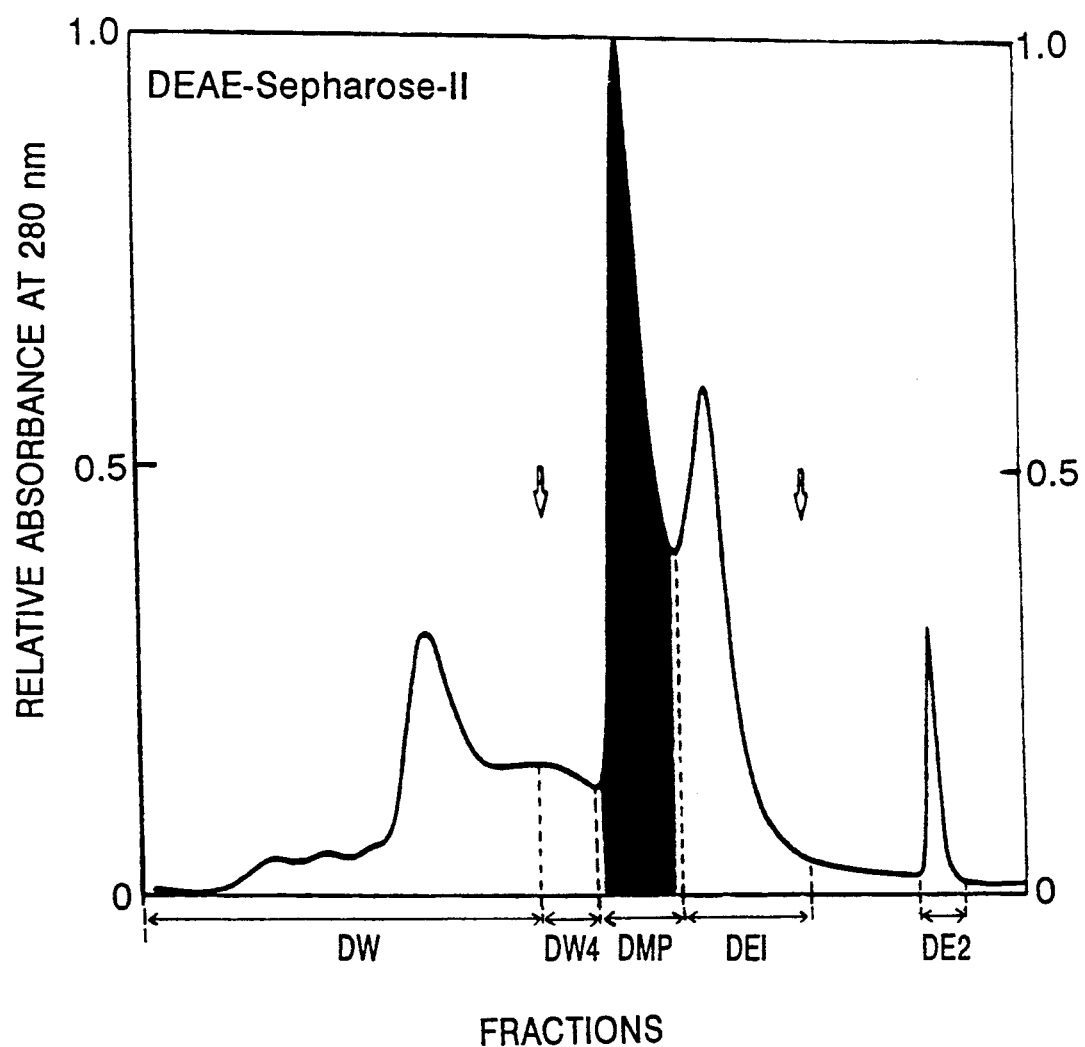
Figure 8A:
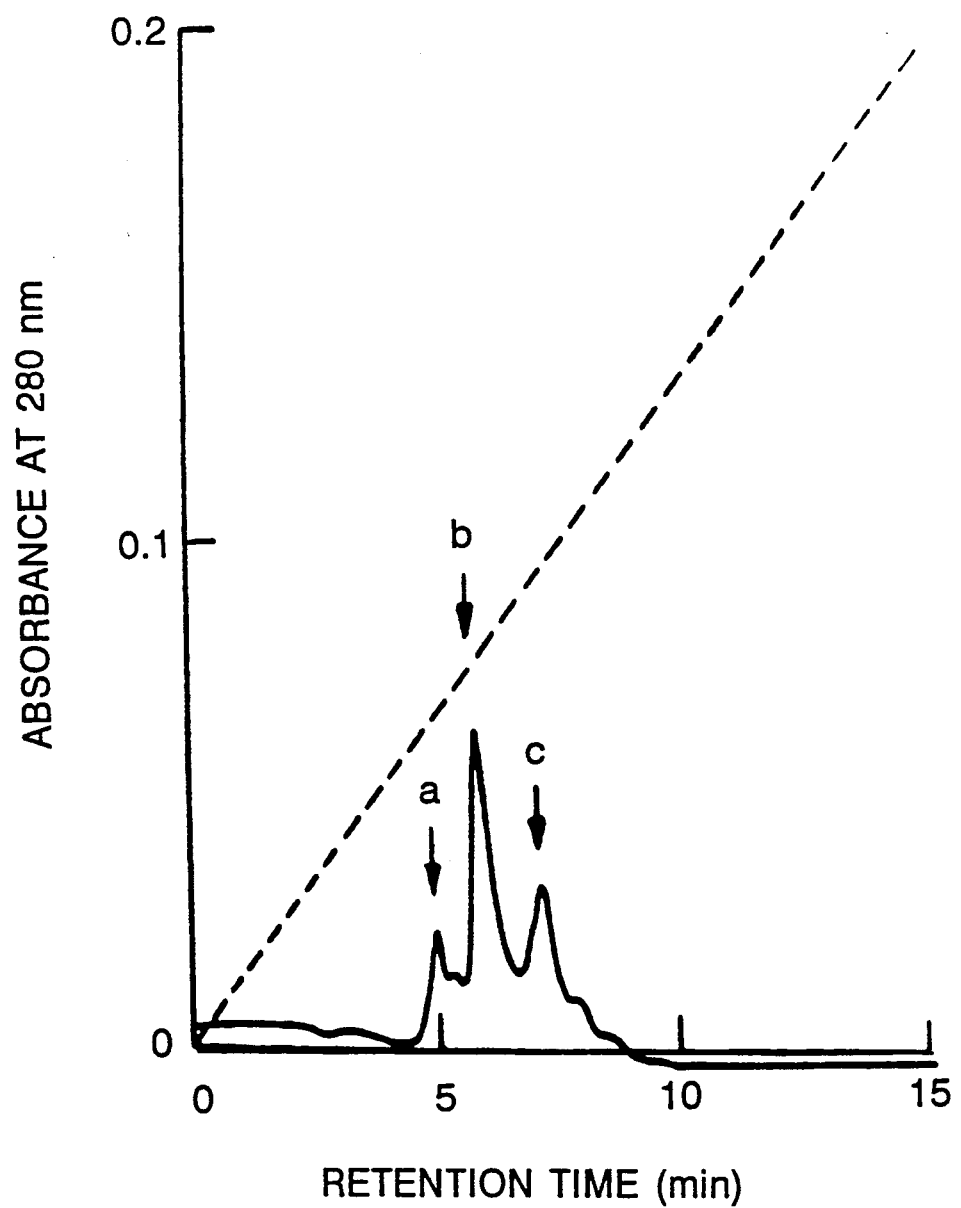
Figure 8B:
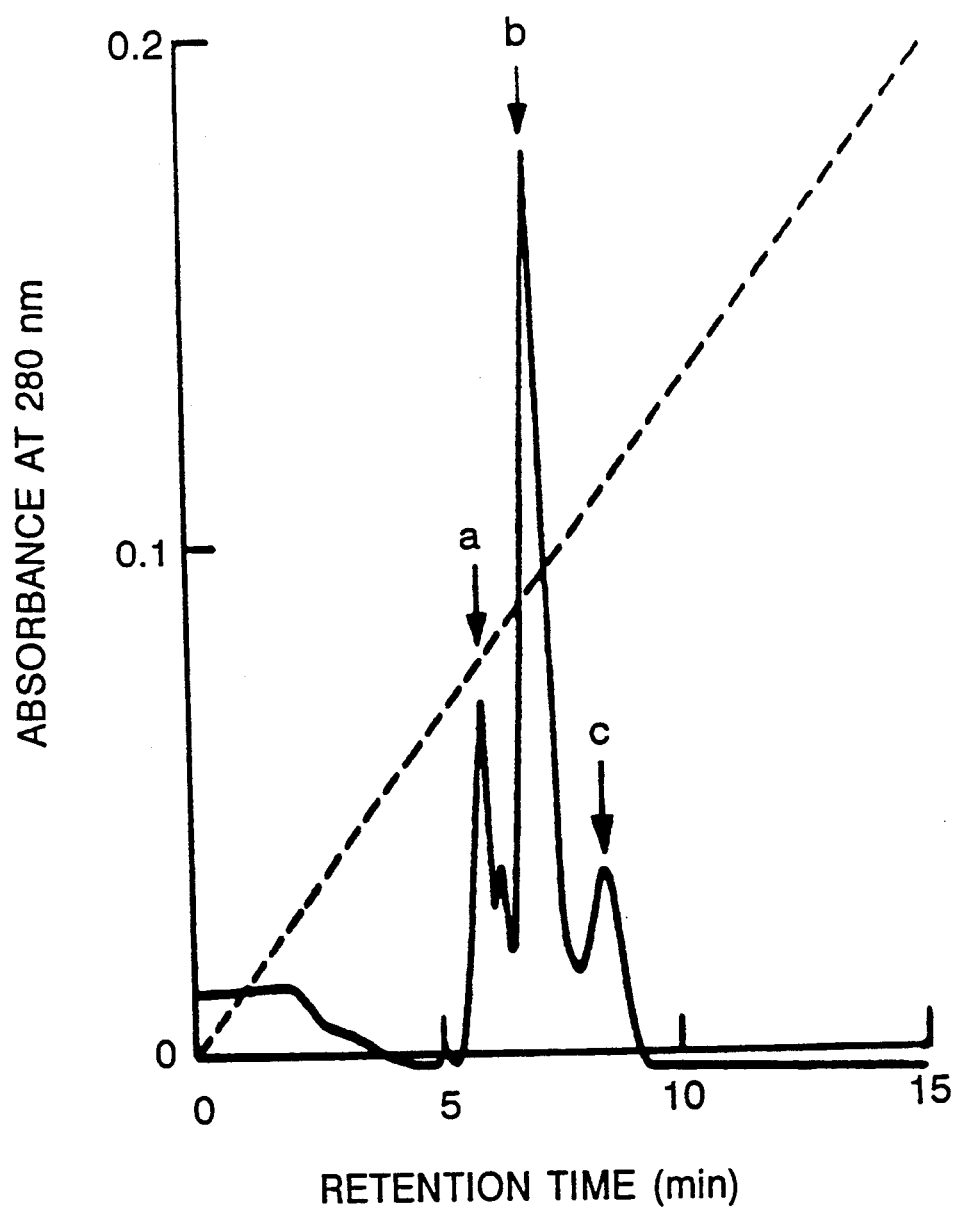

FIG. 8: Analytical fast performance anion exchange chromatography on Mono Q (HR 5/5) column of the fractionated DEAE and CM Sepharose resolved hSOD analog A: a sample from DMP fraction derived from DEAE-Sepharose column (black shaded peak in FIG. 7A) was diluted 1:4 in 20 mM bis Tris-HCl, pH 7.0, and 400 μl were injected onto a Mono Q (HR 5/5) column.

B: a sample from CMP fraction derived from CM-Sepharose column (black shaded peak in FIG. 7B) was adjusted to pH 7.8 with 0.1M NaOH, and 150 μl were injected onto a Mono Q (HR 5/5) column.

The elution conditions of both the columns were as described in FIG. 3.

DETAILED DESCRIPTION OF THE INVENTION

The plasmids designated $pSOD\beta_1T11$, $pSOD\beta$-MAX-12, $pSOD\alpha2$, pMF2005, pMF5534, and pNd-$SOD_{NN}$-12 were deposited pursuant to, and in satisfaction of, the requirements of the Budapest Treaty on the International Recognition of the Deposit of Microorganisms for the Purposes of Patent Procedure with the American Type Culture Collection (ATCC), 12301 Parklawn Drive, Rockville, Md. 20852 under ATCC Accession Nos. 53468, 67177, 39786, 67362, 67703, and 53166, respectively.

The *Escherichia coli* strains designated MC1061, A1645 (containing the plasmid pNd-$SOD_{NN}$-12), A1637 (containing the plasmid pTV104(2)), A2097 (containing the plasmid $pSOD\alpha2$), A4200 (containing the plasmid pHG44), A4255 (containing the plasmid $pSOD\beta MAX$-12), A4048 (containing the plasmid pHG44), S$\phi$930 (containing the plasmid pMF5534), W3110 (containing the plasmid pMFS929), S$\phi$732 (containing the plasmid pMF2005), S$\phi$540 (containing the plasmid pJBF5401), and S$\phi$930 (containing the plasmid pEFF920) were also deposited pursuant to, and in satisfaction of, the requirements of the Budapest Treaty on the International Recognition of the Deposit of Microorganisms for the Purposes of Patent Procedure with the American Type Culture Collection (ATCC), 12301 Parklawn Drive, Rockville, Md. 20852 under ATCC Accession Nos. 67361, 53166, 39384, 39786, 53218, 67177, 53217, 67703, 67705, 67362, 67359, and 67706, respectively.

The subject invention provides a method for recovering a solution containing purified, enzymatically active Cu-Zn superoxide dismutase or a polypeptide analog thereof having substantially the same amino acid sequence as, and the biological activity of, naturally-occurring Cu-Zn superoxide dismutase from a composition which comprises cells containing Cu-Zn superoxide dismutase or a polypeptide analog thereof comprising:

(a) treating the composition so as to separate soluble proteins present in the cells from whole cells, cellular debris and insoluble proteins so as to obtain a solution containing such soluble proteins;

(b) treating the resulting solution containing the soluble proteins with a second solution containing a salt at a concentration such that the soluble proteins other than Cu-Zn superoxide dismutase or the polypeptide analog thereof present in the solution containing the soluble proteins are rendered capable of binding to an appropriate hydrophobic substance;

(c) contacting the then-resulting solution containing the soluble proteins with an appropriate hydrophobic substance so as to bind the soluble proteins other than Cu-Zn superoxide dismutase or the polypeptide analog thereof present in such solution to the hydrophobic substance and thus separate such other proteins from the Cu-Zn superoxide dismutase or polypeptide analog thereof; and (d) recovering the resulting solution containing purified, enzymatically active Cu-Zn superoxide dismutase or polypeptide analog thereof.

The Cu-Zn superoxide dismutase or polypeptide analog thereof may be human Cu-Zn superoxide dismutase or polypeptide analog thereof, for example, the nonacetylated polypeptide analog of human Cu-Zn superoxide dismutase.

It should be understood by a person skilled in the art to which the subject invention pertains that any eucaryotic cell which produces naturally-occurring Cu-Zn superoxide dismutase or polypeptide analogs thereof may be used. The eucaryotic cell may be, for example, a yeast cell or a mammalian cell. The method can also use a bacterial cell.

The bacterial cell in which the Cu-Zn superoxide dismutase or polypeptide analog thereof is produced may be any bacterium in which a DNA sequence encoding the Cu-Zn superoxide dismutase or polypeptide analog thereof has been introduced by recombinant DNA techniques. Of course, the bacteria must be capable of expressing the DNA sequence and producing the desired protein. Presently preferred bacterial cells comprise cells of an *Escherichia coli* strain.

The bacteria may be any strain including auxotrophic, prototrophic and lytic strains; $F^+$ and $F^-$ strains; strains harboring the $cI^{857}$ repressor sequence of the $\lambda$ prophage; and strains deleted for the deo repressors or the deo gene.

Examples of wild type *Escherichia coli* strains which may be used are the prototrophic strain designated ATCC Accession No. 12435 and auxotrophic strain MC1061 (ATCC Accession No. 67361).

Examples of *Escherichia coli* strains harboring the $\lambda$ $cI^{857}$ repressor sequence which may be used are the auxotrophs A1645 containing plasmid pNd-SOD$_{NN}$-12 (ATCC Accession No. 53166), A1637 containing plasmid pTV104(2) (ATCC Accession No. 39384), and A2097 containing plasmid pSODα2 (ATCC Accession No. 39786); and the prototrophs A4200 containing plasmid pHG44 (ATCC Accession No. 53218) and A4255 containing plasmid pSODβMAX-12 (ATCC Accession No. 67177).

Examples of lytic *Escherichia coli* strains which may be used include *Escherichia coli* strain A4048 containing plasmid pGH44 (ATCC Accession No. 53217).

Examples of $F^-$ strains which may be used to express DNA encoding superoxide dismutase are *Escherichia coli* strain Sϕ930 ($F^-$) containing plasmid pMF 5534 deposited under ATCC Accession No. 67703 and *Escherichia coli* strain W3110 ($F^-$) containing plasmid pMFS 929 deposited under ATCC Accession No. 67705; strain W3110 ($F^-$) was obtained from the *Escherichia coli* Genetic Stock Center (C.G.S.C.), Department of Biology, Yale University, P.O. Box 6664, New Haven, Conn., as C.G.S.C. strain No. 4474.

Examples of *Escherichia coli* strains deleted for the deo gene or deo repressors which may be used include Sϕ732 containing plasmid pMF 2005 (ATCC Accession No. 67362), Sϕ540 containing plasmid pJBF 5401 (ATCC Accession No. 67359) and Sϕ930 containing plasmid pEFF 920 (ATCC Accession No. 67706) (see European Patent Application Publication No. 0303972, published Feb. 22, 1989).

The bacterial cell may contain the DNA sequence encoding the superoxide dismutase analog in the body of a vector DNA molecule such as a plasmid. The vector or plasmid is constructed by recombinant DNA techniques, known to those skilled in the art, to have the sequence encoding the superoxide dismutase incorporated at a suitable position in the molecule.

The plasmids used for production of superoxide dismutase can harbor a variety of promoters including but not limited to $\lambda$ promoter or deo promoters.

Among the plasmids which may be used for production of superoxide dismutase are the following:

| Plasmid | Deposited In |
| --- | --- |
| pSODβ$_1$T$_{11}$ | *Escherichia coli* A4255 (ATCC Accession No. 53468) |
| pSODβMAX-12 | *Escherichia coli* A4255 (ATCC Accession No. 67177) |
| pSODα2 | *Escherichia coli* A2097 (ATCC Accession No. 39786) |
| pMF2005 | *Escherichia coli* Sϕ732 (ATCC Accession No. 67362) |
| pMF5534 | *Escherichia coli* Sϕ930 (ATCC Accession No. 67703) |
| pNd-SOD$_{NN}$-12 | *Escherichia coli* A1645 (ATCC Accession No. 53166) |

The treatment of the composition which comprises cells containing Cu-Zn superoxide dismutase or a polypeptide analog thereof so as to separate soluble proteins present in the cells from whole cells, cellular debris and insoluble proteins may comprise treating the composition so as to disrupt the cells and obtain a cellular extract therefrom, and then subjecting the resulting cellular extract to centrifugation so as to obtain the solution containing the soluble proteins.

The cell walls of cultured bacterial cells may be disrupted by any of a number of methods known to those skilled in the art including, but not limited to, high shear mixing, sonication, mechanical disruption, explosion by pressure, osmotic shock, etc.

It should also be understood that the cells may secrete the Cu-Zn superoxide dismutase or polypeptide analog thereof into the medium, such that no cell disruption is required. The cells may then be removed by centrifugation or other means known in the art and the medium used directly for purification of the Cu-Zn superoxide dismutase or polypeptide analog thereof.

The disrupted cell suspension (if disruption is required) may then be centrifuged or separated by other means known to those skilled in the art in order to recover a supernatant containing soluble Cu-Zn superoxide dismutase or polypeptide analog thereof.

In order to precipitate cellular components not containing the superoxide dismutase analog or naturally-occurring superoxide dismutase, the superoxide dismutase solution may subsequently be heated and cooled.

The solution containing soluble proteins, including Cu-Zn superoxide dismutase or polypeptide analog thereof, is treated with a second solution containing a salt at a concentration such that the soluble proteins other than Cu-Zn superoxide dismutase or the polypeptide analog thereof present in the solution containing the soluble proteins are rendered capable of binding to an appropriate hydrophobic substance. The salt may be any suitable salt known in the art. Suitable salts which may be used include sodium sulphate and sodium chloride, although ammonium sulphate is preferred. Other salts which may be used include potassium chloride and ammonium acetate. Any combination of the foregoing salts may also be used.

The final salt concentration depends on, and is characteristic of, the salt which is used. For ammonium sulphate, the final salt concentration varies from 1.2–1.9M and is preferably 1.6M; for sodium sulphate, the concentration range may vary between 0.9–1.25M, preferably 1.0M; and for sodium chloride the range is 3.0–4.5M, preferably 4.0M. Optimal salt concentration ranges for other salts may be readily ascertained by those skilled in the art.

The appropriate hydrophobic substance preferably comprises prises phenyl Sepharose. The appropriate hydrophobic substance may also comprise a suitable resin having a phenyl functional group, preferably a polysaccharide resin having phenyl groups present thereon. The contact with the hydrophobic substance preferably is effected by passing the solution containing the soluble proteins through a column containing the hydrophobic substance.

Any hydrophobic column may be used, preferably phenyl-Sepharose. The functional group may be phenyl, benzyl, octyl, butyl and the matrix may be any of those discussed below.

The soluble proteins other than Cu-Zn superoxide dismutase or the polypeptide analog thereof in the solution are bound to the hydrophobic substance in the column, thus separating the Cu-Zn superoxide dismutase or polypeptide analog thereof from the other soluble proteins. The resulting solution containing purified, enzymatically active Cu-Zn superoxide dismutase or polypeptide analog thereof is then recovered.

In one preferred embodiment, the method described above for recovering a solution containing purified, enzymatically active Cu-Zn superoxide dismutase or a polypeptide analog thereof further comprises the following steps prior to the treatment with a second solution containing a salt:

The resulting solution containing the soluble proteins, after its separation from whole cells, cellular debris and insoluble proteins, is treated so as to obtain a more concentrated solution containing purified Cu-Zn superoxide dismutase or polypeptide analog thereof.

Preferably, the treatment of the solution to obtain a more concentrated solution of purified Cu-Zn superoxide dismutase or polypeptide analog thereof comprises ultrafiltration.

The ultrafiltration techniques are known to those skilled in the art. The exact filtration conditions, such as permeate flow rate and filter cut-off range are not critical and may be readily ascertained by a person skilled in the art of protein purification. Various systems which may be used include, but are not limited to, a PUF-100 Unit and a Pellicon Cassette System (Millipore).

Ultrafiltration may be further conducted using a smaller molecular weight cut-off. It should be understood that the particular molecular weight cut-off used or the order used for various molecular weight cut-off filters is not critical to an understanding of the invention.

The Cu-Zn superoxide dismutase present in the more concentrated solution may comprise a, b and c isoforms of Cu-Zn superoxide dismutase or polypeptide analog thereof. The resulting more concentrated solution of purified Cu-Zn superoxide dismutase or polypeptide analog thereof is then treated so as to produce three separate solutions, each of which has an increased concentration of one of either of the a, b or c isoform.

Preferably, the treatment of the concentrated solution comprises anion exchange chromatography.

The then-resulting solution which has an increased concentration of the b isoform of purified Cu-Zn superoxide dismutase or polypeptide analog thereof is subjected to cation exchange chromatography so as to produce three further separate solutions, each of which has a further increased concentration of one of either of the a, b or c isoform.

The then-resulting solution which has a further increased concentration of the b isoform of purified Cu-Zn superoxide dismutase or polypeptide analog thereof is then treated so as to further purify the Cu-Zn superoxide dismutase or polypeptide analog thereof contained therein prior to treating the resulting solution containing the further purified Cu-Zn superoxide dismutase or polypeptide analog thereof with a second solution containing a salt.

Preferably, the treatment of the then-resulting solution comprises strong anion exchange chromatography, preferably by passing the then-resulting solution through a column of a polysaccharide resin having quaternary amino functional groups present thereon.

Examples of a strong anion exchange column which may be used include Q-Sepharose and QAE Sephadex A-25. Functional groups may be any quaternary amino group such as quaternary amino ethyl and the matrix may be any of those discussed below.

Furthermore, the then-resulting solutions which have an increased or further increased concentration of one of either of the a or c isoform may be treated so as to increase the concentration of b isoform and reduce the concentration of a isoform and c isoform of the polypeptide analog contained in each of the solutions prior to treating the then-resulting solution containing the further purified Cu-Zn superoxide dismutase or polypeptide analog thereof with a second solution containing a salt in step (b).

Preferably, the treatment of the then-resulting solutions prior to step (b) comprises:

(a) combining the separate solution which has an increased concentration of the a isoform with the separate solution which has an increased concentration of the c isoform;

(b) treating the resulting combined solution so as to produce a solution which has an increased concentration of the b isoform;

(c) recovering the then-resulting solution which has an increased concentration of the b isoform.

Preferably, the treatment of the resulting combined solution so as to produce a solution which has an increased concentration of the b isoform comprises incubation.

The solutions with an increased concentration of the b isoform from step (b) can further be treated so as to purify the b isoform present in the solutions. Preferably, the treatment of the solution comprises ion exchange chromatography. The ion exchange chromatography may comprise anion exchange chromatography and further comprise cation exchange chromatography.

In one preferred embodiment, after treating the resulting solution with a second solution containing a salt and contacting the then-resulting solution with an appropriate hydrophobic substance, the resulting solution containing purified, enzymatically active Cu-Zn superoxide dismutase or polypeptide analog thereof is recovered. The recovered resulting solution may then be treated so as to obtain a more concentrated solution containing purified Cu-Zn superoxide dismutase or polypeptide analog thereof.

Preferably, the treatment of the recovered resulting solution to obtain a more concentrated solution of purified Cu-Zn superoxide dismutase or polypeptide analog thereof comprises ultrafiltration.

The resulting more concentrated solution containing purified Cu-Zn superoxide dismutase or polypeptide analog thereof may then be treated so as to obtain a solution containing more purified Cu-Zn superoxide dismutase or polypeptide analog thereof.

Preferably, the treatment of the resulting solution comprises strong anion exchange chromatography, preferably by passing the resulting solution through a column of a polysaccharide resin having quaternary amino functional groups present thereon.

In another preferred embodiment, after treating the resulting solution with a second solution containing a salt and contacting the then-resulting solution with an appropriate hydrophobic substance, the resulting solution containing purified, enzymatically active Cu-Zn superoxide dismutase or polypeptide analog thereof is recovered and treated so as to obtain a solution containing more purified Cu-Zn superoxide dismutase or polypeptide analog thereof.

Preferably, the treatment of the resulting solution comprises strong anion exchange chromatography, preferably by passing the resulting solution through a column of a polysaccharide resin having quaternary amino functional groups present thereon.

In yet another preferred embodiment, the resulting solution containing the soluble proteins, after its separation from whole cells, cellular debris and insoluble proteins, is treated so as to purify the Cu-Zn superoxide dismutase or polypeptide analog thereof contained therein prior to treating the resulting solution containing the soluble proteins with a second solution containing a salt.

Preferably, the treatment of the resulting solution comprises strong anion exchange chromatography, preferably by passing the resulting solution through a column of a polysaccharide resin having quaternary amino functional groups present thereon.

In another preferred embodiment, the method described above for recovering a solution containing purified, enzymatically active Cu-Zn superoxide dismutase or a polypeptide analog thereof further comprises treating the resulting solution containing the soluble proteins, after its separation from whole cells, cellular debris, and insoluble proteins (the soluble proteins including Cu-Zn superoxide dismutase or polypeptide analog thereof comprising a, b and c isoforms of Cu-Zn superoxide dismutase or polypeptide analog thereof) so as to increase the concentration of b isoform and reduce the concentration of a isoform and c isoform of the polypeptide analog contained in the solution prior to treating the resulting solution containing the soluble proteins with a second solution containing a salt.

Preferably, the treatment of the resulting solution containing the soluble proteins prior to treatment with a second solution containing a salt comprises:

(a) treating the resulting solution containing the soluble proteins so as to produce three separate solutions, each of which has an increased concentration of one of either of the a, b, or c isoform:

(b) recovering the separate solution which has an increased concentration of the b isoform;

(c) combining the separate solution which has an increased concentration of the a isoform with the separate solution which has an increased concentration of the c isoform;

(d) treating the resulting combined solution so as to produce a solution which has an increased concentration of the b isoform; and (e) recovering the then-resulting solution which has an increased concentration of the b isoform.

Preferably, the treatment of the resulting combined solution so as to produce a solution which has an increased concentration of the b isoform comprises incubation.

Furthermore, the treatment of the resulting solution so as to produce three separate solutions preferably comprises ion exchange chromatography.

It will be appreciated by those skilled in the art that any number of ion exchange columns may be used including weak anion exchange, cation exchange or so-called "strong anion" exchange columns. In addition, it will be appreciated by one skilled in the art that the protein purification using ion exchange chromatography may involve applying a high concentration of solution through an anion exchange followed by a cation exchange, or a cation exchange followed by an anion exchange or an anion exchange followed by an anion exchange or a cation exchange followed by a cation exchange. Moreover, only one exchange, i.e., either cation or anion, may be required.

The anion exchange of this method and the method disclosed above may involve, for example, a DEAE Sepharose fast-flow column and the cation exchange may involve, for example, a CM Sephadex or S-Sepharose column.

Weak anion exchange columns used usually have a tertiary amine, e.g., diaminoethyl, as a functional group, although amino ethyl may also be used. The matrix may be based on inorganic compounds, synthetic resins, polysaccharides organic polymers. Examples of matrices which may be used include agarose, cellulose, trisacryl, dextran, glass beads, oxirane acrylic beads, acrylamide, agarose/polyacrylamide copolymer (Ultragel) and hydrophobic vinyl polymer (Fractogel).

Examples of cation columns which may be used instead of carboxymethyl (CM) Sepharose fast flow include CM Sephadex or S Sepharose columns. Functional groups which may be used include carboxymethyl, phospho groups or sulphonic groups such as sulphopropyl. Any of the matrices discussed above for weak anion exchange columns may be used in cation exchange columns as well.

Additionally, the solution with an increased concentration of the b isoform which is recovered can further be treated so as to purify the b isoform present in the solution. Preferably, the treatment of the solution comprises ion exchange chromatography. The ion exchange chromatography may comprise anion exchange chromatography, and may further comprise cation exchange chromatography.

Using the invention described above, the contaminating *Escherichia coli* or bacterial proteins and endotoxins are reduced by about one-thousand fold.

While not wishing to be bound by theory, it appears that the critical step leading to reduction in contaminating ECP is the hydrophobic separation step following the optional anion and cation exchange chromatography steps. This hydrophobic separation step is novel. In this hydrophobic separation step, it is the desired superoxide dismutase protein which passes through the hydrophobic column while undesirable *Escherichia coli* proteins are absorbed. The use of such a step in the purification procedure surprisingly and unexpectedly leads to a marked decrease in the level of contamining *Escherichia coli* proteins.

The invention also provides a novel method involving subunit exchange for increasing the yield of recovered solutions having an increased concentration of b isoform of an enzymatically-active polypeptide analog of Cu-Zn superoxide dismutase from a composition which comprises cells containing a, b and c isoforms of the polypeptide analog which comprises:

(a) treating the composition so as to separate soluble proteins present in the cells from whole cells, cellular debris and insoluble proteins so as to obtain a solution containing such soluble proteins, including the a, b and c isoforms;
 (b) treating the resulting solution containing the soluble proteins so as to produce three separate solutions, each of which has an increased concentration of one of either of the a, b or c isoform;
 (c) recovering the separate solution which has an increased concentration of the b isoform;
 (d) combining the separate solution which has an increased concentration of the a isoform with the separate solution which has an increased concentration of the c isoform;
 (e) treating the resulting combined solution so as to produce a solution which has an increased concentration of the b isoform; and
 (f) recovering the then-resulting solution which has an increased concentration of the b isoform.

The rationale behind this procedure is that a certain percentage of Cu-Zn superoxide dismutase protein is normally discarded during the purification process and in particular during the cation and anion exchange chromatography steps discussed above. More particularly, various isoforms of human superoxide dismutase, i.e., the a and c isoforms, contain high amounts of contaminating *Escherichia coli* proteins (ECP) and therefore peaks containing these isoforms are discarded, along with the ECP after the chromatography step. Peaks containing the b isoform are kept for further processing. According to the protocol of this invention, peaks containing predominantly a and c isoforms are combined and incubated to form b isoforms which may then be used for further purification downstream.

Preferably, the treatment of the resulting combined solution so as to produce a solution which has an increased concentration of the b isoform comprises incubation.

The polypeptide analog of Cu-Zn superoxide dismutase may be a polypeptide analog of human Cu-Zn superoxide dismutase.

Preferably, the treatment of the composition so as to separate soluble proteins present in the cells from whole cells, cellular debris and insoluble proteins comprises treating the composition so as to disrupt the cells and obtain a cellular extract therefrom, and then subjecting the resulting cellular extract to centrifugation so as to obtain the solution containing the soluble proteins.

Preferably, the treatment of the resulting solution containing the soluble proteins so as to produce three separate solutions comprises ion exchange chromatography.

In a preferred embodiment, the method further comprises treating the solution with an increased concentration of the b isoform from step (c) or (f) so as to purify the b isoform present in the solution. Preferably, the treatment of the solution comprises ion exchange chromatography. The ion exchange chromatography may comprise anion exchange chromatography and may further comprise cation exchange chromatography.

EXAMPLES

The examples which follow are set forth to aid in understanding the invention but are not intended to and should not be construed as to limit its scope in any way.

Example 1

Detailed Description of the hSOD Expression Plasmid (pSODβ₁T11)

The plasmid used for production of hSOD analog is plasmid pSODβ₁T11 FIG. 1).

The construction of plasmid pSODβ₁T11has been fully described in coassigned, copending European patent application publication no. 0173280, published on May 5, 1986 (corresponding to U.S. patent application Ser. No. 644,105, filed Aug. 27, 1984, issued May 2, 1988 as U.S. Pat. No. 4,742,004). This plasmid contains the following elements:

(a) the origin of replication of plasmid pBR322;
 (b) the Tet$^R$ gene of plasmid pBR322 in counterclockwise orientation; and
 (c) in clockwise orientation and in 5' to 3' order, the λ P$_L$O$_L$ promoter/operator region, the β-lactamase promoter and ribosomal binding site and the coding sequence for hSOD analog.

Plasmid pSODβ₁T11 is a high level expressor of hSOD analog protein under the control of the strong leftward promoter of bacteriophage λ (P$_L$) which is thermoinducibly controlled by the cI857 temperature sensitive repressor situated on the host chromosome.

Plasmid pSODβ₁T11 was used to transform prototrophic *Escherichia coli* strain A4255, and the resulting bacterium is used for production of hSOD analog. Prototrophic *Escherichia coli* strain A4255 was prepared from prototrophic *Escherichia coli* strain ATCC Accession No. 12435 (obtained from the ATCC collection) by transfection with Tn10 transposon carrying defective λ prophage (cI857 ΔH1 ΔBam N⁺) and subsequently deleted for tetracycline resistance gene (carried by Tn10). *Escherichia coli* strain A4255 containing plasmid pSODβ₁T11 was deposited in the ATCC under Accession No. 53468.

Example 2

Growth of *Escherichia coli* strain No. A4255 containing plasmid pSODβ1T11-production of bacterial cake containing hSOD analog 1. Preparation of Frozen Stock Culture The bacteria producing hSOD analog (*Escherichia coli* strain No. A4255/pSODβ₁T11) are cultivated overnight at 30° C. in shake flasks containing CAS medium, which is of the following composition:

| | |
|---|---|
| Casein hydrolysate | 20 g |
| Yeast extract | 10 g |
| NaCl | 5 g |
| Deionized water | 1 L |

12.5 mg/L sodium tetracycline HCl is also added to the flasks at the time of inoculation.

Following incubation, an aliquot of the stationary-phase culture (having an optical density at 660 nm of between 6-12) is thoroughly mixed with an equal volume of sterile freezing medium, containing the following:

| | |
|---|---|
| $K_2HPO_4$ | 6.3 g |
| $KH_2PO_4$ | 1.8 g |
| Sodium citrate | 0.45 g |
| $MgSO_4.7H_2O$ | 0.09 g |
| $(NH_4)_2SO_4$ | 0.09 g |
| Glycerol, 87% | 44 g (50 ml) |
| Deionized water | 450 ml |

The cell suspension is dispensed in 2 ml aliquots into sterile, plastic screw-top vials (Nunc Cryo-tubes, cat. No. 3-63401, or equivalent) and frozen at $-70°$ C. until use.

2. Inoculum

The inoculum is propagated in 20 g/L casein hydrolysate, 10 g/L yeast extract, 5 g/L NaCl, and 12.5 mg/L tetracycline HCl. Sterile medium in shaker flasks is inoculated from stock culture and incubated 8-10 hours on a shaker at 30° C. at approximately 240 rpm. The flask contents are used to inoculate the seed fermentor.

3. Seed Fermentor

The seed fermentor medium is identical to production medium (see below) except that all the glucose (30 g/L) is added at the start of fermentation; the medium lacks added copper and zinc. Sterile medium is inoculated with culture, and incubated 15 hours at 30° C., pH $7\pm0.1$ with agitation and aeration to maintain a dissolved oxygen level of about 20% saturation. Contents of the seed fermentor are then transferred to the production fermentor.

4. Production Fermentor

The production medium contains:

| | |
|---|---|
| Casein hydrolysate | 20 g/L |
| Yeast extract | 10 g/L |
| $K_2HPO_4$ | 2.5 g/L |
| $MgSO_4.7H_2O$ | 1 g/L |
| NaCl | 5 g/L |
| Antifoam (Silicone) | 0.4 ml/L |
| Glucose | 30 g/L |
| $CuSO_4.5H_2O$ | 0.49 g/L |
| $ZnSO_4.7H_2O$ | 0.009 g/L |

Sterile glucose solution is added initially to supply 10 g/L. During the course of the fermentation, an additional 20 g/L is supplied. The medium is inoculated with 5-10% seed culture and incubated at 30° C. Agitation-aeration rates are set to maintain a dissolved oxygen level of about 20% air saturation. The pH is maintained at $7.0\pm0.1$ with $NH_3$. Once cell concentration reaches about 6.5 g/L ($OD_{660}=16$) induction is started by raising the temperature to 42° C. The temperature is maintained at 42° C. for 2 hours, at which time the cells are harvested from the cell suspension.

5. Harvest of Bacterial Cake

Five hundred liters of cell suspension (containing 12 DCW/L and 200 mg hSOD/L) obtained as described in Section 4 is cooled to room temperature and transferred to a holding tank. The cell suspension is centrifuged at 14,000 rpm (16,000×g) in a CEPA 101 tubular bowl centrifuge at a feed rate of 250 liters/hr. The CEPA 101 centrifuge has a tube length of 73.7 cm, a radius to the discharge dam of 3.25 cm and a radius to the bowl wall of 7.35 cm. It is equipped with acceleration fins and has cooling on the exterior jacket.

The clear supernatant has a density of 1.0 g/ml, contains no detectable hSOD analog and is discarded. The cake, weighing 16 kg (75% wet), contains hSOD analog and is washed.

6. Washing of Bacterial Cake

The cake obtained as described above is resuspended in 25 mM potassium phosphate buffer, pH 7.8, containing 155 mM NaCl. The composition of the buffer is:

| | |
|---|---|
| Deionized water | 1.0 L |
| NaCl | 9 g |
| $K_2HPO_4$ | 4.0 g |
| $KH_2PO_4$ | 0.3 g |

7 L buffer is used per kg net weight of cake. The cake is suspended in the buffer, mixed thoroughly, and then centrifuged in the CEPA 101 centrifuge at a feed rate of 150 L/hr. The supernatant contains no detectable hSOD analog and is discarded. The cake, weighing 16 kg and containing the hSOD analog, is saved.

Example 3

Improved Method for Purification of Recombinant Cu-Zn hSOD Analog

The following method gives greatly improved yield and purity of the hSOD analog. The general scheme of the downstream process (Scheme I) consists of steps A through I, as follows:

| Scheme I - Downstream Processing of the Recombinant Human Cu-Zn SOD Analog | |
|---|---|
| (A) | CELL DISRUPTION |
| (B) | HEAT TREATMENT |
| (C) | 100K ULTRAFILTRATION |
| (D) | 10K ULTRAFILTRATION |
| (E) | DEAE CHROMATOGRAPHY |
| (F) | CM CHROMATOGRAPHY |
| (G) | PHENYL-SEPHAROSE (PS) CHROMATOGRAPHY (HYDROPHOBIC CHROMATOGRAPHY) |
| (H) | Q SEPHAROSE (QS) CHROMATOGRAPHY |
| (I) | FREEZE DRYING and PACKAGING |

The following detailed example of the steps in purification of the Cu-Zn hSOD analog is a scaled-up example involving hundreds of grams of product. It should be understood that the following is a preferred method only and that the invention is not limited to specific embodiments described or particular order of steps recited.

A. CELL DISRUPTION

Harvested cell cakes are weighed and stored frozen at $-20°$ C. Cakes weighing 50-60 kg from one or more fermentations are processed downstream.

The wet cell cake (51.6 kg containing 260 gr hSOD analog) is thawed at 4°–10° C. and suspended in 4 liters of 25 mM Tris-75 mM NaCl buffer pH 7.8 for each kilogram of wet cells (total volume of suspension is 258 liters). A Polytron high-shear mixer (Kinematica, Luzern) aids in dispersing the cake. The pH of the suspension is adjusted to 7.3–7.5 if necessary. The suspended cells are then disrupted by any suitable method, e.g., by sonication or mechanical disruption. The following method is preferred. The cells are fed into a Dynomill KD-5 bead mill disrupter (Willy A. Bachofen, Basel) at 80 L/hr. The bead mill is circulated with a cooling liquid at −20° C. to maintain the temperature of the bead mill discharge at 8°–25° C. The bead mill discharge is fed again into the Dynomill and grinding of the suspension is repeated according to the above conditions. The pH of the disrupted cell suspension is adjusted to 7.3–7.5 if necessary. The suspension is centrifuged on the Cepa 101 tubular bowl centrifuge (Carl Padberg, Lahr/Schwarzwald) at 14,000 rpm (16,000 G's). The feed rate to the centrifuge is 45–55 L/hr. The cake (weighing 23.4 kg) is discarded. The supernatant (243 L) contains the soluble hSOD analog and is saved.

Disruption Conditions:
Dynomill Model KD-5
Speed 1810 rpm
Bead diameter 0.25 to 0.50 mm or 0.50 to 0.75 mm
Shell volume 4.2 L
Centrifuge Conditions:
Cepa 101 Centrifuge
Tube length 73.70 cm
Radius to discharge dam 3.25 cm
Radius to bowl wall 7.35 cm
Typical cake thickness 2.0 cm
Speed 14,000 rpm-16,000 G's
Inlet temperature 30° C.
Outlet temperature 35° C.
Cooling on exterior jacket
Acceleration fins-yes NOTE: Temperatures quoted above result from use of frozen or thawed cells at 4°–10° C. It may be assumed that temperatures up to 37° C. are not harmful to the hSOD analog.

B. HEAT TREATMENT

The supernatant from the previous step (243 L containing 250 gr hSOD) is supplemented with 0.25N NaCl by adding 5N NaCl providing a final concentration of 0.325N NaCl and the pH is adjusted to 7.3–7.5 if necessary.

The solution is transferred into a jacketed bioreactor (Bioengineering AG., Wald, Switzerland). An ICI Silcolapse 5000 antifoam is added to a final concentration of 10–15 ppm active material. The temperature is raised at a slow rate to 65° C. while stirring gently to avoid foaming. The heat treatment at 65° C. is carried out for 2 hours and terminated by cooling the solution in the bioreactor to 40° C. and then transferred to a cold room for incubation at 4° C. overnight (10–16 hours) without stirring.

The cooled solution is centrifuged on the Cepa-101 at 40–60 L/hr. All other centrifugation conditions are identical to those of cell disruption. The cake (weighing 11.3 kg) is discarded. The clarified supernatant (233 L) containing the soluble hSOD analog is saved and the pH is adjusted to 7.3–7.5.

C. 100K ULTRAFILTRATION (PUF-100 UNIT)

Any ultrafiltrate method with a cut-off point at 100K may be used in this step. Examples of such methods are the Pellicon cassette system or Amicon's hollow fiber system. The preferred ultrafiltration method is the Millipore PUF-100 Unit, Process Ultrafiltration System equipped with two 50 ft$^2$ spiral-wound membrane cartridges with 100,000 molecular weight cut-off ratings (Millipore Intertech, Inc., Bedford, Mass.). This is used to concentrate the protein solution of the previous step (230 L containing 232 gr hSOD) to about 10% of the initial volume (20 L) and the filtrate (210 L containing some of the hSOD) is saved. The initial permeate rate is 6 L/min. The retentate containing the rest of the hSOD is diafiltered by continuous addition of fresh 20 mM Tris buffer at pH 7.8 to the well-mixed retentate at a rate just equal to the permeate rate. In this way the volume of retentate remains constant while the hSOD passes through the membrane. Diafiltration is continued until 2–3 times the volume of the clarified protein solution used in the beginning of this step is collected (460 liters of filtrate). At this point the permeate OD is checked and found to be in the range 0.1–0.2. [During this period, the membranes are depolarized several times whenever a decrease in permeate flow rate is observed (below 4 L/min). This is achieved by diluting the retentate to 40 liters and recirculating for a few minutes with the permeate valves shut off. The retentate is concentrated again to 20 liters and diafiltration resumes.] The filtrate is collected, combined with the permeate (210 L) of the concentration step (total of 670 L) and the retentate is discarded.

Ultrafiltration conditions:

| Membrane - PTHK cartridges | | |
|---|---|---|
| | Initial | Final |
| Inlet Pressure - psig | 10 | 12 |
| Outlet Pressure - psig | 6 | 10 |
| Recirculation rate | | |
| L/min | 40 | 60 |
| L/hr-ft$^2$ | 24 | 36 |
| Permeate rate | | |
| L/min | 6 | 4 |
| L/hr-ft$^2$ | 3.6 | 2.4 |

The feed, retentate and permeate are all examined by Superose 6B gel chromatography in order to determine the extent and quality of the separation. The conditions of the gel column are:

| 1.6-cm dia. × 55-cm long (Pharmacia, Uppsala) | |
|---|---|
| Total volume: | 110 ml |
| Void volume: | 30 ml |
| Flow rate: | 60 ml/hr |
| Loading: | |
| Feed: | 20–25 OD's in 0.25 ml |
| Retenate: | 3–5 OD's in 0.25 ml |
| Permeate: | 4–6 OD's in 0.25 ml |
| Eluent: | 20 mM Tris - 150 mM NaCl, pH 7.8 |
| Normal running time: | 2.3 hours |
| Detection: | 280 nm UV |

The 100K molecular weight cut off fractionation of hSOD analog has been practiced by ultrafiltration with both the PUF-100 Unit and the Pellicon Cassette System. The Pellicon System is suitable for smaller batches of hSOD, as described below. The cell cake weight of this batch was 9.25 Kg containing 45 gr hSOD analog.

The clarified protein solution obtained at the end of the heat treatment step (44 liters containing 41.6 gr hSOD) is ultrafiltered through two Pellicon Cassette Systems each of them equipped with five 100,000 molecular weight cut-off cassettes (type PTHK) of 5 ft² area each (Millipore Intertech, Inc., Bedford, Mass.). The protein solution is concentrated to about 10% of the initial clarified protein solution volume (5.5 L of retentate) and the permeate is saved. The retentate is diafiltered by continous addition of fresh 20 mM Tris solution at pH 7.8 to the well-mixed retentate at a rate just equal to the permeate rate. In this way the volume of retentate remains constant while the hSOD passes through the membrane. Diafiltration is continued until the permeate has an absorbance at 280 nm (1-cm cell) of less than 0.2. This normally produces 2-3 times the volume of the clarified protein solution (150 L permeate). The permeates of the concentration and diafiltraton steps are combined (190 L containing 40.5 gr hSOD analog) while the retentate is discarded.

Ultrafiltration Conditions:

| Millipore Pellicon System | | |
|---|---|---|
| Membrane: | PTHK cassette (100K cut-off) | |
| Inlet Pressure: | 50 psig | |
| Backpressure: | 5-8 psig | |
| | | UF rate with 10 cassettes (50 ft²) |
| Ultrafiltration rate when retentate is most concentrated | 3.6 L/hr ft² | 180 L/hr |
| Ultrafiltration rate when retentate is most dilute | 4.2 L/hr ft² | 210 L/hr |
| Recirculation rate when retentate is most concentrated | 12 L/hr ft² | 10 L/min |
| Recirculation rate when retentate is most dilute | 14.4 L/hr ft² | 12 L/min |

D. 10K ULTRAFILTRATION (PUF-100 UNIT)

Any ultrafiltration method with a cut-off point of 10K may be used in this step. The preferred method is described here, where a Millipore PUF-100 unit and a Pellicon Cassette System (10K cut-off) are used sequentially.

The combined permeate from the previous step (670 L containing 229 gr hSOD) is inline fed into a Millipore PUF-100 Unit, Process Ultrafiltration System equipped with two 50 ft² spiral-wound membrane cartridges with 10,000 molecular weight cut-off ratings (Millipore Intertech, Inc., Bedford, Mass.), and the permeate rate is checked. The initial permeate rate is 9 L/min. The solution is concentrated to 2-5% (20 L) of the permeate combined volume. The retentate is then diafiltered by continously adding fresh 20 mM Tris buffer at pH 7.8 to the well-mixed retentate at a rate just equal to the permeate rate. In this way, the volume of retentate remains constant and the hSOD analog is retained while lower molecular weight proteins pass through the membrane. [During this period, the membranes are depolarized several times whenever a decrease in permeate flow rate is observed (below 4 L/min). This is achieved by diluting the retentate to 40 liters and recirculating for a few minutes with the permeate valves shut off. The retentate is concentrated again to 20 liters and diafiltration resumes.] The diafiltration is completed when the permeate conductivity is equal to that of the diafiltration buffer (at least 20 volumes per volume of retentate are required). The retentate is drained out of the PUF-100 Unit container and transferred for a final concentration through a Pellicon Cassette System equipped with three 10K molecular weight cut off cassettes (type PTGC) of 5 ft² area each (Millipore Intertech, Inc., Bedford, Mass. The hSOD analog is concentrated to a maximum of 100 gr/L (10 L containing 229 gr). The retentate is drained out of the Pellicon and the ultrafilter is washed with a small amount of 20 mM Tris pH 7.8 which is combined with the retentate.

The combined retentate volume after addition of the wash is divided into portions containing an amount equivalent to about 75 gr hSOD analog each (3 portions) which are processed directly or stored at −20° C. Prior to proceeding to the next purification step, frozen hSOD analog solutions are thawed at 37° C.

(a) PUF-100 UNIT

| Membrane: PTCG Cartridges | | |
|---|---|---|
| | Initial | Final |
| Inlet Pressure: psig | 25 | 25 |
| Outlet Pressure: psig | 20 | 20 |
| Recirculation Rate: | | |
| L/min. | 50 | 50 |
| L/hr-ft² | 30 | 30 |
| Permeate Rate: | | |
| L/min. | 9 | 4.5 |
| L/hr-ft² | 5.4 | 2.7 |

(b) PELLICON CASSETTE SYSTEM

| Membrane: | PTCG Cartridges |
|---|---|
| Inlet Pressure: | 20-30 psig |
| Backpressure: | 5-10 psig |

UF Concentration Conditions:

| | | UF rate with 3 cassettes (15 ft²) |
|---|---|---|
| Ultrafiltration rate when retentate is most concentrated | 6 L/hr ft² | 90 L/hr |
| Ultrafiltration rate when retentate is most dilute | 8 L/hr ft² | 120 L/hr |
| Recirculation rate when retentate is most concentrated | 54 L/hr ft² | 13.5 L/min |
| Recirculation rate when retentate is most dilute | 36 L/hr ft² | 9.0 L/min |

The retentate and permeate are examined by Superose 6B gel chromatography to determine the extent and quality of the separation.

The conditions of the gel column are:

| Loading: | |
|---|---|
| Retentate: | 30-40 OD's in 0.25 ml. |
| Permeate: | 3-4 OD's in 0.25 ml. |

All other gel column conditions are identical to those described in the 100K ultrafiltration step (PUF-100 Unit).

E. DEAE CHROMATOGRAPHY

Any weak anion exchange (e.g. tertiary amine) method can be used in this step but DEAE Sepharose fast-flow chromatography is preferred.

From this step on, protein solutions obtained in the preceding manner from several runs can be combined and processed downstream. The amount of hSOD analog which is processed at each step is a function of the equipment capacity.

Figure 2A:
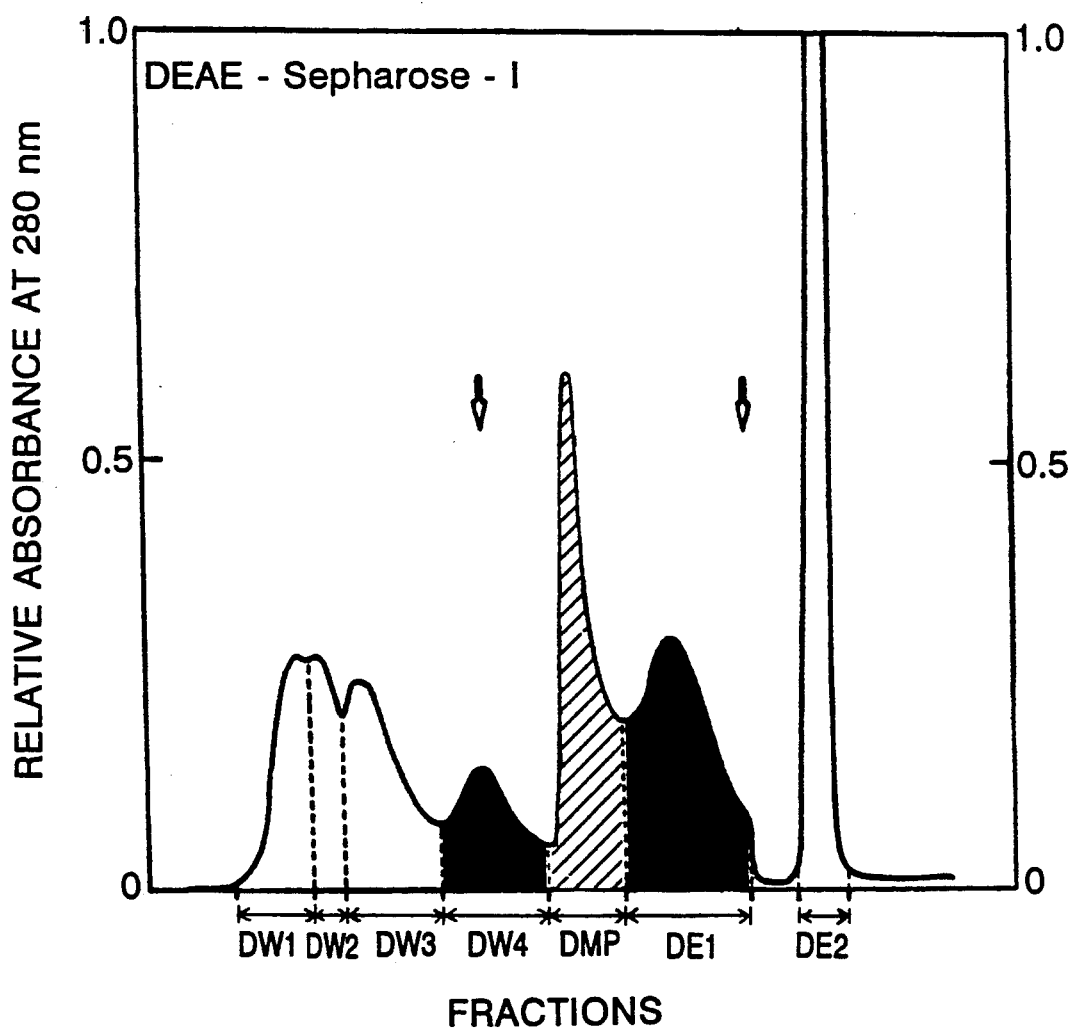

A retentate solution from the previous step (3300 ml of 23 mg hSOD analog/ml) is diluted to 10 mg hSOD/ml with 20 mM Tris, pH 7.8. The solution is loaded onto a KS-370 stack column [37 cm×15 cm (Pharmacia, Uppsala)], packed with 16 L of DEAE Sepharose Cl-6B fast flow anion exchanger at a maximum linear flow velocity of 164 cm/hr (180 L/hr). An equivalent of 75 gr hSOD analog maximum is loaded onto 16 liters of resin without peak separation interference. From this step on, pyrogen-free water purified by reverse osmosis system (Hydro-Hammer, Tel Aviv) is used. The progress of the run is monitored by continuously following the absorbance of the eluate at 280 nm and the elution profile of this column is shown in FIG. 2A. The column is washed at the above flow rate with three to four bed volumes (48–64 L) of 20 mM Tris-25 mM NaCl at pH 7.8 until the blue peak is fully eluted. The eluate from the loading and washing steps is discarded (however, see Example 4). A step change in eluent to 20 mM Tris-80 mM NaCl at pH 7.8 displaces the hSOD analog off the column; this is the peak shaded in black in FIG. 2A. The elution flow velocity is up to 180 L/hr and the hSOD analog peak is collected in 0.8 to 1.5 bed volumes (21 liters containing 50 gr hSOD) and is saved. The average concentration of the hSOD analog in the pool is approximately 2.5 gr hSOD/L.

Concentration after DEAE:

The eluted peaks from one or more loadings are concentrated by ultrafiltration through a Millipore Pellicon Cassette System equipped with three 10,000 molecular weight cut-off cassettes (type PTGC) of 5 ft$^2$ each until the calculated activity in the retentate is up to 100 mg hSOD/ml. The ultrafiltrate should contain no hSOD analog and is discarded. The retentate is usually concentrated by a factor of roughly 20 (2 liters of retentate).

After the hSOD analog has been concentrated, the retentate containing the hSOD analog is drained from the Pellicon, and the ultrafilter is washed with a small amount of 20 mM Tris pH 7.8 which is combined with the retentate. The combined retentate volume after addition of the wash is divided into portions each containing not more than an equivalent of 75 gr hSOD analog and that is processed directly or stored at −20° C. Prior ro proceeding to the next purification step, frozen hSOD solutions are always thawed at 37° C.

Ultrafiltration Conditions:

| Millipore Pellicon System | | |
|---|---|---|
| Membrane: | PTGC (10K cut-off) | |
| Inlet Pressure: | 20–30 psig | |
| Backpressure: | 10 psig | |
| | | UF rate with 3 cassettes (15 ft$^2$) |
| Ultrafiltration rate when retentate is most concentrated | 4.8 L/hr ft$^2$ | 72 L/hr |
| Ultrafiltration rate when retentate is most dilute | 6.4 L/hr ft$^2$ | 96 L/hr |
| Recirculation rate when retentate is most concentrated | 54 L/hr ft$^2$ | 13.5 L/min |
| Recirculation rate when retentate is most dilute | 36 L/hr ft$^2$ | 9.0 L/min |

F. CM CHROMATOGRAPHY

In this step any cation exchange method can be used, e.g. CM Sephadex or S-Sepharose. The preferred method is carboxymethyl (CM) Sepharose Fast Flow (FF).

A retentate solution from the previous step (4000 ml containing 21.15 mg hSOD analog/ml) is dialyzed on the day of loading onto the CM column.

The dialysis is carried out by continuously adding 40 mM sodium acetate at pH 7.8 to the retentate using the Millipore Pellicon Cassette System. All other concentration and dialysis conditions are identical to those described in the DEAE Chromatography step. The dialysis is completed when the filtrate conductivity is equal to that of the dialysis buffer (20–25 volumes per volume of retentate). The permeate is discarded. The retentate is drained out of the Pellicon and the ultra-filter is washed with a small amount of 40 mM sodium acetate pH 7.8 which is combined with the retentate.

Figure 2B:
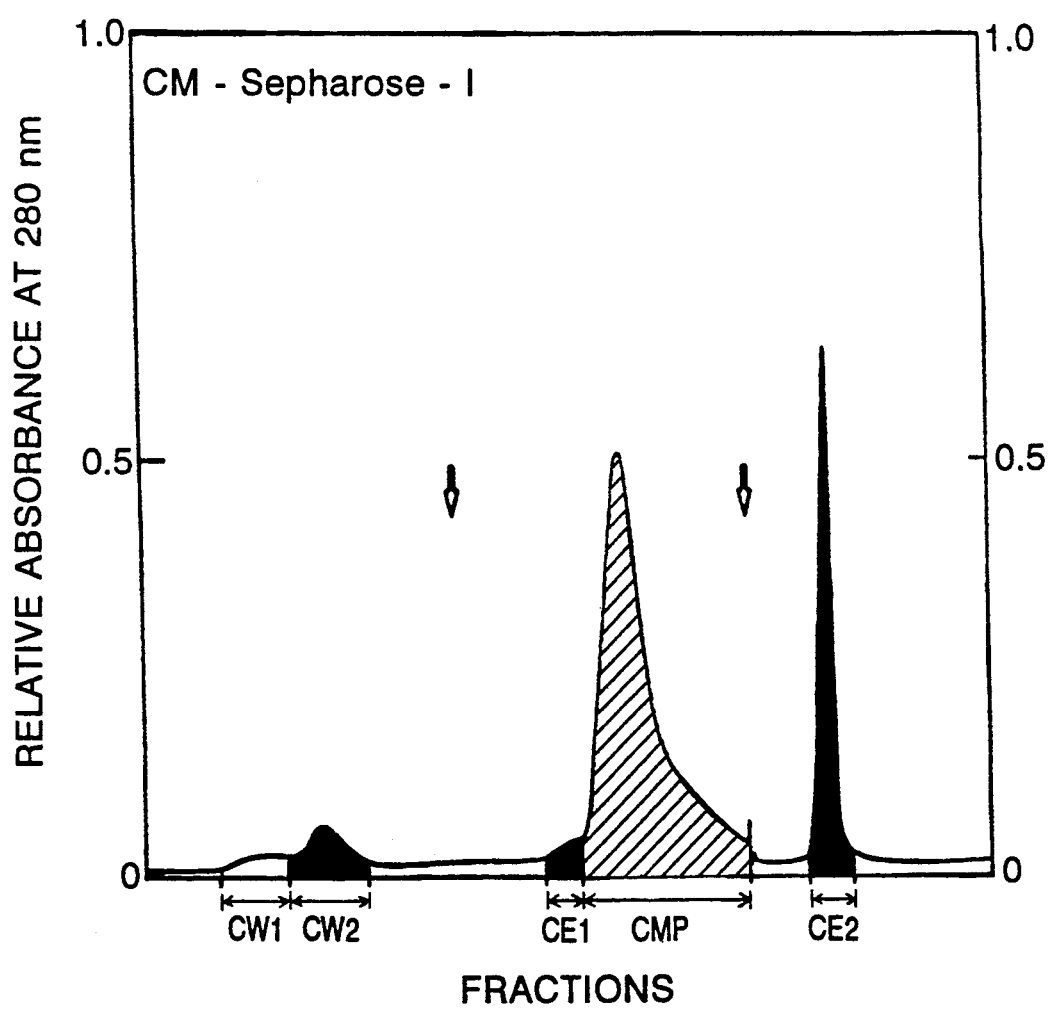

An equivalent of about 75 gr hSOD analog of retentate solution (2000 ml containing 31.25 mg hSOD/ml) is adjusted to pH 4.8 by adding 1M glacial acetic acid. Then the solution is diluted to 10 mg hSOD/ml with 40 mM sodium acetate pH 4.8 and immediately loaded onto a KS-370 stack column [37 cm×15 cm (Pharmacia, Uppsala)], packed with 16 L of CM Sepharose Cl-6B fast flow cation exchanger at a linear flow velocity of up to 164 cm/hr (180 L/hr). Up to 75 gr hSOD analog can be loaded onto 16 L of resin. The progress of the run is monitored by continuously following the absorbance of the eluate at 280 nm, and the elution profile of this column is shown in FIG. 2B.

The column is washed at the above flow rate with three to four bed volumes (48–64 L) of 40 mM sodium acetate adjusted to pH 4.8 with glacial acetic acid. The eluate from the loading and washing steps is discarded (however, see Example 4). A step change in eluent to 85 mM sodium acetate adjusted to pH 4.8 with glacial acetic acid displaces the hSOD analog off the column; this is the peak shaded in black in FIG. 2B.

The maximum elution flow velocity is 180 L/hr and the hSOD analog peak is collected in 0.75 to 1.25 bed volume (12 L) and is saved. The protein solution is titrated immediately to pH 7.8 with 1N NaOH.

At this point in the process most of the impurities have been eliminated and U.V. absorbance fairly monitors hSOD analog concentration.

Concentration and dialysis after CM:

The eluted peaks from one or more loadings carried out on the same day are concentrated up to 100 mg hSOD analog/ml. The concentration conditions are identical to those described in the DEAE Chromatography step. The retentate is then dialyzed against 50 mM Tris pH 7.8 using the Millipore Pellicon Cassette System. The dialfiltration is performed until the permeate conductivity is equal to that of the dialysis buffer (at least 20 volumes of dialysis buffer per one volume of retentate are required).

The retentate containing the dialyzed hSOD analog is drained from the Pellicon and the ultrafilter is washed with a small amount of 50 mM Tris pH 7.8 which is combined with the retentate. The combined retentate is divided into portions of 150–160 gr hSOD analog, each of which are processed directly or stored at −20° C.

Ultrafiltration Conditions:

| Millipore Pellicon System | |
|---|---|
| Membrane: | PTGC (10K cut-off) |
| Inlet Pressure: | 20–30 psig |
| Backpressure: | 10 psig |

UF Diafiltration Conditions

| | | UF rate with 3 cassettes (15 ft$^2$) |
|---|---|---|
| Ultrafiltration rate | 4.8 L/hr ft$^2$ | 72 L/hr |
| Recirculation rate | 54 L/hr ft$^2$ | 13.5 L/min |

G. PHENYL - SEPHAROSE (PS) CHROMATOGRAPHY

In this step phenyl-Sepharose chromatography is used to achieve hydrophobic separation. The hSOD analog, which is applied in overcapacity and in high salt concentration, does not attach to the column but goes straight through; this achieves purification of hSOD analog from residual *Escherichia coli* protein (ECP) and endotoxin which are absorbed. This novel step achieves a surprising degree of reduction of ECP and endotoxin contamination. The ECP levels are reduced by about 3 orders of magnitude; the measurement of ECP by a solid-phase immunoradiometric assay is described in Example 5 where the reduction of ECP by means of the phenyl-Sepharose column is detailed (Table 2). The endotoxin level is reduced by a similar extent, from about 10,000 ppm to less than 10 ppm, as measured by the Limulus Amebocyte Lysate (LAL) assay described in U.S. Pharmacopeia (U.S.P.) XXI 1165–1166 (1985).

A retentate solution from the previous step (5000 ml containing 31.6 mg hSOD analog/ml), is brought by 50 mM Tris pH 7.8 to a protein concentration of 25–30 mg hSOD/ml. A buffer containing 50 mM Tris-3.2M ammonium sulfate at pH 7.8 is used to dilute volume per volume the proteinaceous solution to a final concentration of 12.5 to 15 mg hSOD analog/ml (15 mg hSOD/ml is preferable) in 1.6M ammonium sulfate and 50 mM Tris at pH 7.8. The solution is stirred gently for 30–60 minutes at room temperature and then loaded on a 11.3×30 cm column (113 Bioprocess, Pharmacia, Uppsala) packed with 3 L of phenyl-Sepharose fast flow at a linear flow velocity of 3–6 L/hr. A maximum of 150 gr hSOD analog can be loaded on the 11.3×30 cm column. The column is eluted by 50 mM Tris-1.6M ammonium sulfate, fate, pH 7.8 which displaces the hSOD analog off the column. The elution flow velocity is 3–6 L/hr. The progress of the run is monitored continuously by following the absorbance of the eluate at 280 nm. The eluted hSOD analog peak has maximal absorbance after about one and one-half bed volume of eluant. Material eluted at the beginning of the peak (up to 2% of the maximum absorbance) is discarded. The major portion of the peak is saved (from where the absorbance is 2% of the maximum absorbance at the beginning of the peak to 5% of the maximum at the end (9–12 L)).

Concentration and Dialysis After Phenyl-Sepharose

The eluted peak is concentrated by ultrafiltration through a Millipore Pellicon Cassette System equipped with three 3000 molecular weight cut-off cassettes of 5 ft$^2$ each until the calculated activity in the retentate is up to 25 mg hSOD analog/ml. The ultrafiltrate should contain no hSOD and is discarded. The retentate is then dialyzed against 20 mM Tris pH 8.8. The dialysis is completed when the filtrate pH and conductivity are equal to that of the dialysis buffer (at least 20 volumes per volume of retentate are needed). The retentate containing the dialyzed hSOD analog is drained from the Pellicon and the ultrafilter is washed with a small amount of 10 mM ammonium bicarbonate, pH 8.0 which is combined with the retentate. All mentioned ultrafiltration activities are performed in a cold room (4°–10° C.). The combined retentate (5460 ml containing 23.9 hSOD/ml) can be transferred to the next step or stored frozen at −20° C.

UF Diafiltration Conditions

| Millipore Pellicon System | |
|---|---|
| Membrane: | 3K cut-off (Filtron, Massachusetts, USA) |
| Inlet Pressure: | 20–30 psig |
| Backpressure: | 5–10 psig |

| | | UF rate with 3 cassettes (15 ft$^2$) |
|---|---|---|
| Ultrafiltration rate when retentate is most concentrated | 4.8 L/hr ft$^2$ | 60 L/hr |
| Ultrafiltration rate when retentate is most dilute | 6.4 L/hr ft$^2$ | 30 L/hr |
| Recirculation rate when retentate is most concentrated | 25.2 L/hr ft$^2$ | 6.3 L/min |
| Recirculation rate when retentate is most dilute | 16.8 L/hr ft$^2$ | 4.2 L/min |

H. Q-SEPHAROSE (QS) CHROMATOGRAPHY

In this step a strong anion exchanger is used. This can be, for example, QAE Sephadex A-25, but the preferred method is to use Q-Sepharose (QS). Note also that the order of Steps G and H can be interchanged, but the order given here is preferred. It is also possible for the superoxide dismutase analog solution to be of sufficient purity after the hydrophobic column exchange step that this step may be unnecessary.

The retentate solution from the previous step (3.88 L of 28.6 mg hSOD analog/ml) is diluted to 5 mg hSOD analog/ml with 20 mM Tris, pH 8.8 and supplemented with 20 mM NaCl. The solution is stirred gently at 20°–30° C. for 30–45 minutes and loaded on a KS 370 stack column (37×15 cm, Pharmacia, Uppsala) packed with 16 L of Q-Sepharose fast flow anion exchanger, at a linear flow velocity of 90–180 L/hr. A maximum of 200 gr hSOD analog can be loaded on the KS 370 column. The column is washed with one to two bed volumes of 20 mM Tris-45 mM NaCl, pH 8.8 and the eluate is discarded. A step change in eluent to 20 mM Tris-130 mM NaCl, pH 8.8 displaces the hSOD analog off the column. The elution flow velocity is 90–180 L/hr. The progress of the run is monitored continuously by following the absorbance of the eluate at 280 nm. The eluted hSOD analog peak has maximal absorbance after about one bed volume of eluent. The major portion of the peak (50–60 liters) is saved. Material eluted at the end of the peak (where the absorbance is lower than 5% of the maximal absorbance) is discarded.

Concentration and dialysis after QS:

The eluted peak is concentrated to an OD of up to 45 then dialyzed against 10 mM ammonium bicarbonate pH 8.0 using the Millipore Pellicon Cassette System in a cold room (5° C.). The dialysis is completed when the filtrate pH and conductivity are equal to that of the dialysis buffer (at least 20 volumes per volume of retentate are needed). All other concentration and dialysis conditions are identical to those described in the DEAE and the CM Chromatography steps. The retentate containing the dialyzed hSOD analog is drained from the Pellicon and the ultrafilter is washed with a small amount of 10 mM ammonium bicarbonate, pH 8.0 which is combined with the retentate. The combined retentate wash (2.34 L of 44.45 mg hSOD analog/ml) is transferred to the next step.

I. FREEZE DRYING AND PACKAGING

Freeze drying of the bulk hSOD analog is carried out as follows: The hSOD analog solution is diluted using 10 mM ammonium bicarbonate, pH 8.0 to a final concentration of 7 to 10 mg hSOD/ml (10.4 L of 10 mg hSOD/ml) and then divided into approximately 600 ml fractions under aseptic conditions in a laminar flow hood (Contamination Control Inc., Lansdale, Pa.). Each portion is added to a 2 liter glass jar preheated for 4 hours in a 180° C. oven. The jars are frozen quickly using an acetone-dry ice mixture and put on a freeze dryer (Freezemobile-24, Virtis Company, New York). The outer surface of the jars is exposed to ambient temperature for 60-120 hours throughout the drying cycle until the hSOD analog is dry, and it is then packaged.

The overall yield of hSOD analog is about 25% and it is extremely pure, containing less than 10 ng ECP per mg hSOD analog.

Increase in yield with no loss of purity may be achieved by following the procedure described in Example 4.

Example 4

A Novel Procedure for Improving the Yield of Cu-Zn hSOD Analog Production by Means of Subunit Exchange The following novel procedure may be used as an addition to the purification protocol described in Example 3 (Scheme I). It significantly increases the yield of hSOD analog without affecting the required high degree of purification achieved and with relatively low additional cost.

A. RATIONALE FOR THE EXCHANGE PROCEDURE

Cu-Zn SOD enzymes from different species consist of dimers built from two chemically identical subunits and yet are known to appear in several discrete forms on isoelectric focusing gel (IEF). The existence of electroforms of various Cu-Zn SOD enzymes have been reported (1-8) and recently reviewed by I. Fridovich (9).

As demonstrated by IEF analysis and FPLC/Mono-Q anionexchange chromatography, the dimeric human Cu-Zn SOD can be separated into three major electroforms. The electroforms (or isoforms) may represent post-translation modifications.

The IEF and Mono-Q patterns of natural Cu-Zn hSOD can be explained in terms of there being two types of subunits, which can result in one or two extra negative charges per dimer. These differences in charge provide the different pI values. The subunits designated x and y could associate to yield xx, xy and yy dimers which would correspond to the observed three major dimeric isoforms, designated a, b, and c, respectively.

We have shown by IEF analysis and also by analytical Mono-Q anion exchange chromatography that the recombinant hSOD analog also consists of three discrete isoforms with pIs of 5.16, 4.95, and 4.85 that are the a, b and c isoforms, respectively. The Cu-Zn hSOD that has been extracted from red blood cells also has three isoforms with pIs of 4.85, 4.75, and 4.65 i.e., natural hSOD is more acidic than the recombinant Cu-Zn hSOD analog. The acidic shift appearing in the IEF pattern of the authentic hSOD versus the recombinant analog can be explained by the net decrease of two positive charges at the N-terminal residues of the authentic Cu-Zn hSOD which are blocked by one N-acetyl group per polypeptide chain (1, 6, 10).

The question remains as to the chemical nature of the different isoforms. We postulate, although not wishing to be bound by theory, that the cause for charge heterogeneity might be due to residue modification at position Cys-111 of one or both subunits. It is known that Cu-Zn SOD enzymes from different sources have different pI values (6, 9). Moreover, studies have shown that intraspecies hybridization of Cu-Zn SOD subunits can be performed and the reformed hybrid SOD dimer has an intermediate electrophoretic mobility on isoelectrofocusing gels compared to the "parental" dimers (2–5).

We have shown that the recombinant Cu-Zn hSOD analog can undergo subunit exchange of the different dimeric isoforms and this is described below; we have also shown that the recombinant hSOD analog can hybridize to authentic Cu-Zn SOD from human and bovine sources.

We isolated the three isoforms denoted a, b, and c of the recombinant hSOD analog (FIGS. 3A, 5A and 3B, respectively). Incubation of a mixture of equal amounts of isolated isoforms a and c produced a mixture which contained about 50% of the hybridized b isoform and about 25% each of the a and c isoforms (FIG. 3F). The new b isoform is produced by random hybridization between one subunit derived from the a dimer and one subunit derived from the c dimer. Thermal incubation proved to be the best method for the hybridization (FIG. 3, D-F and FIG. 4).

The reversibility of the subunit exchange phenomenon can be demonstrated by heat incubation of isolated isoform b produced by hybridization of isolated a and c isoforms; the re-formation of a and c isoforms to a level of about 25% each is shown (FIG. 5).

The column procedures for hSOD analog purification (Scheme I) are described in Example 3, steps E and F (DEAE Sepharose and CM Sepharose respectively). During the hSOD analog purification, the b isoform becomes predominant and the a-rich and c-rich fractions, which contain relatively high amounts of Escherichia coli proteins (ECP) and which run on either side of the main hSOD analog peak, are preferentially discarded. In FIGS. 2A and 2B, these a-rich and c-rich peaks are shaded black.

We have invented a novel protocol in which these previously discarded fractions from DEAE and CM-Sepharose are collected, mixed together in the right proportions and incubated under conditions which effect the maximum amounts of conversion of the a and c isoforms into the b isoform through the subunit exchange mechanism. The reconstituted b dimer can then be recovered and repurified on DEAE and CM columns before it is added to the main batch (see FIGS. 6, 7, 8). This novel procedure significantly raises the recovery of HSOD analog without affecting the purity of the product.

B. DETAILED PROCEDURE i. DEAE Sepharose Column (see Example 3E).

The elution profile of this column is shown in FIG. 2A; the main b-rich hSOD analog peak is hatched. The peak (shaded black) appearing immediately prior to the main hSOD peak is a-rich. This material mostly elutes in the wash step with 20 mM Tris, 25 mM NaCl, pH 7.8. The peak which follows the main hSOD peak is shown to be c-rich (also shaded black). In our new purification protocol these two samples (which are normally discarded) are collected and treated as described below.

ii. CM Sepharose Column (see Example 3F)

The elution profile of this column is shown in FIG. 2B; the main b-rich hSOD analog peak is hatched. The two peaks appearing prior to the main hSOD peak are c-rich, and these peaks are shaded black. This material elutes in the wash step with 40 mM sodium acetate pH 4.8. The peak eluting later, on the addition of 0.5M NaCl, is a-rich; this peak is also shaded black. In our new purification protocol these two c-rich and a-rich samples (which are normally discarded) are now collected and treated as described below.

iii. The bulk hSOD analog preparation is kept at the end of step F in Example 3 for the a-rich and c-rich samples to be treated.

iv. All four additional samples, two from the DEAE-Sepharose column (i) and two from the CM-Sepharose column (ii), are treated as follows: each sample is first concentrated by ultrafiltration, as described in Example 3 step E, and then dialyzed against 20 mM tris pH 7.8. The four samples are then combined.

v. Incubation of the combined samples is performed under conditions that can be varied e.g., 4 hours at 37° C., or 2 hours at 37° C. followed by overnight at room temperature, or 30 minutes at 50° C. All three sets of incubation conditions have a fairly similar effect on the formation of the intermediate isoform b by means of subunit exchange from isoforms a and c. The kinetics of formation of the new b isoform is temperature dependent.

Figure 7B:
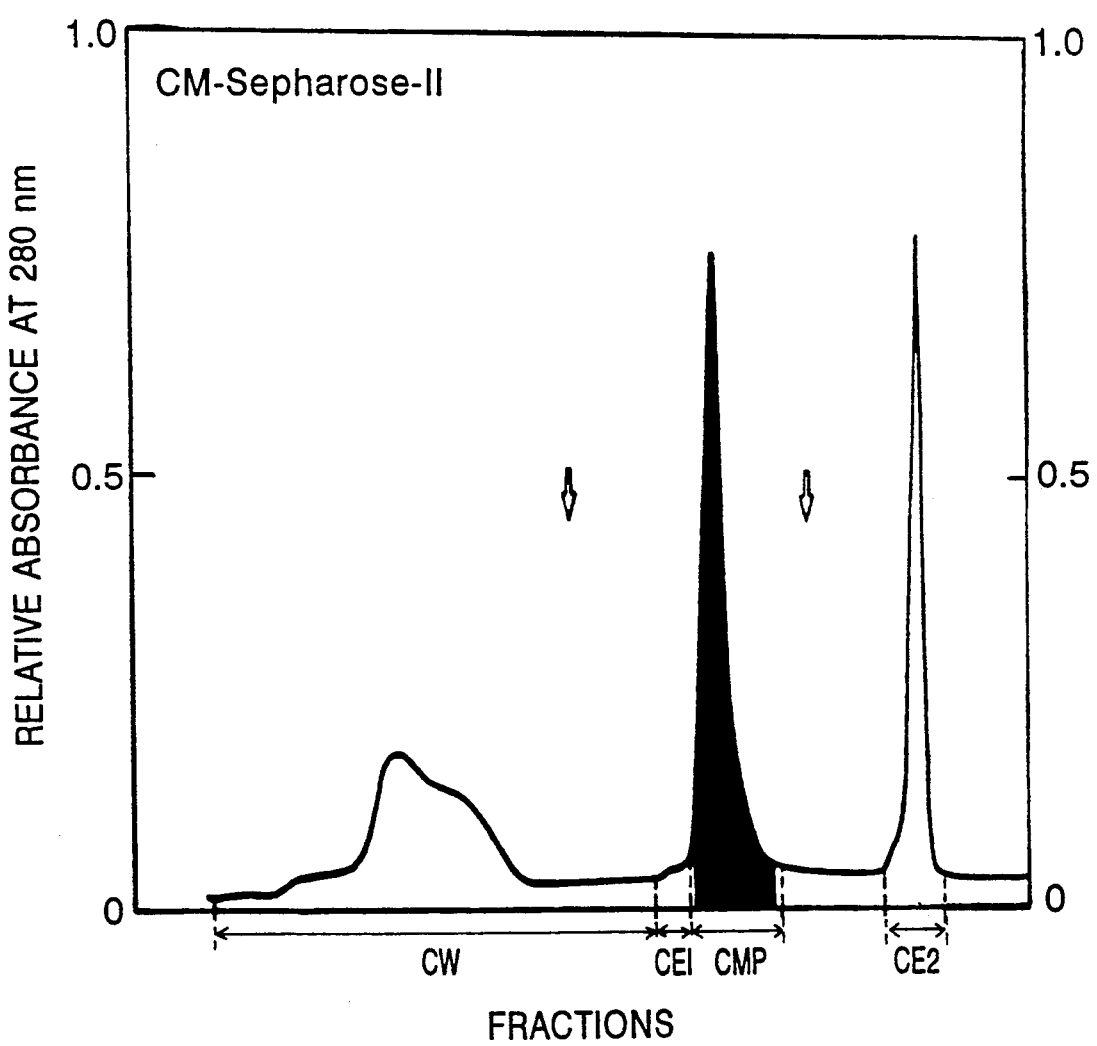

The amount of the new b dimer formed is, of course, dependent on the relative amounts of a and c dimers added to the incubation mixture. Thus, the proportion in which the four samples are mixed is critical for the overall success of the exchange process.

vi. Following the incubation the mixture becomes b-rich (FIG. 6). At the end of the exchange step, the material is chromatographed on DEAE-Sepharose and on CM-Sepharose (i.e. steps E and F of Example 3 are repeated); this re-chromatography is shown in FIGS. 7A and B. This purified preparation is then added to the bulk preparation held at step F(iii). Steps G, H and I are then performed on the combined material as one batch.

The novel procedure described herein is shown in Scheme II, shown on the next page. The recombinant Cu-Zn hSOD analog produced is as pure as that achieved by Scheme I (described in Example 3) and the yield is increased from the level of 25% achieved by Scheme I to 33% achieved by Scheme II.

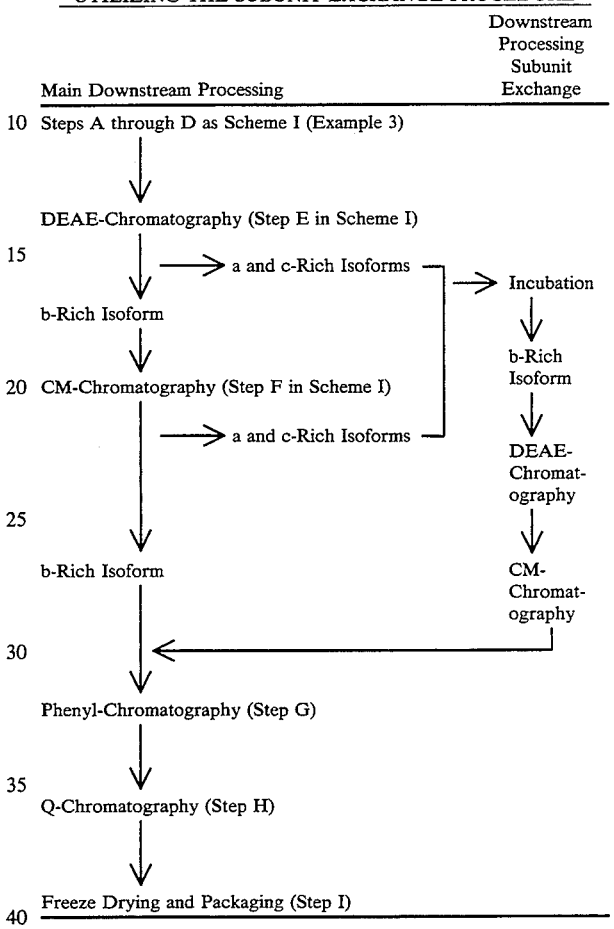

SCHEME II
DOWNSTREAM PROCESSING OF THE RECOMBINANT HUMAN CU—ZN SOD ANALOG UTILIZING THE SUBUNIT EXCHANGE PROCEDURE

Example 5

Detection of *Escherichia coli* Protein (ECP) Contaminants in Purified SOD Analog By a Solid-Phase Immunoradiometric Assay The purpose of this assay is to quantify residual ECP presence in the purified recombinant hSOD analog preparation. In order to evaluate ECP appropriately, we developed an immunoradiometric assay (IRMA) that shows a high degree of specificity and sensitivity.

The ECP standard was prepared from a mock purification process (Example 3) of *Escherichia coli* reference (*Escherichia coli* containing the plasmid without the gene coding for hSOD analog); the fraction used was that which eluted from the CM-Sepharose column. Antibody to this ECP was raised in rabbits and purified IgG's to the ECP were obtained.

The solid-phase IRMA is accomplished by first coating the wells of a plastic 96-well plate with purified IgG's against the mock-purified, CM-eluted ECP fraction. CM-purified ECP, at serial dilutions, is allowed to bind to the IgG in the wells. Subsequently, $^{125}$I-labeled anti-ECP antibody is added, thereby providing a "sandwich" complex which allows accurate and sensitive assessment of binding and the construction of an ECP standard curve.

TABLE I

STANDARD CURVE: TITRATION OF ECP

| ppm | cpm (triplicates) |
|---|---|
| 20,000 | 5093; 5046; 5142 |
| 10,000 | 4320; 4344; 4349 |
| 5,000 | 4255; 4213; 4268 |
| 2,500 | 4056; 4006; 4038 |
| 1,250 | 3198; 3209; 3222 |
| 625 | 2916; 2910; 2897 |
| 312.5 | 2661; 2663; 2640 |
| 156.25 | 2440; 2496; 2468 |
| 78 | 2284; 2288; 2276 |
| 39 | 2131; 2280; 2175 |
| 19.5 | 2051; 2028; 2175 |
| 9.76 | 1960; 1935; 1948 |
| 4.88 | 1870; 1848; 1835 |
| 2.44 | 1842; 1830; 1828 |
| Buffer | 1824; 1816; 1815 |

Based on this curve, the IRMA proved to be sensitive to 1 ng/ml of ECP, which is significantly different from the zero point, as defined by the minimum detectable dose method of Rodbard et al., Radioimmunoassay And Related Procedures In Medicine I (International Atomic Energy Agency, Vienna) p. 469, (1977).

The above assay was used to monitor the ECP in various steps of hSOD analog purification. The antigen used was produced at Step F after the CM column. (See Example 3, Scheme I.) As can be seen from the results shown below, (Table 2) the two subsequent steps G and H (phenyl-Sepharose chromatography and Q-Sepharose chromatography) remove efficiently virtually all ECP contaminants from the SOD analog preparation. Note that here steps G and H are reversed. This is a possible alternative order, as described in Example 3.

TABLE II

Measurement of ECP levels after various stages in purification of recombinant hSOD analog.

| Stage in Purification | Corresponding Stage in Example 3 | ECP (ppm) |
|---|---|---|
| DEAE Sepharose Chromatography | E | 14,700 |
| CM Sepharose Chromatography | F | 4,350 |
| Q-Sepharose Chromatography | H | 1,900 |
| Phenyl-Sepharose Chromatography | G | 1.5 |

Example 6

Preparation Of Naturally-Occurring Cu-Zn Superoxide Dismutase From Liver

A homogenized human liver preparation was heat-treated at 65° C. and then centrifuged. Ammonium sulphate was added to the supernatant solution and the 65%–80% ammonium sulphate precipitate was obtained. A solution of this precipitate was applied to a DEAE ion-exchange column to separate the manganese superoxide dismutase (MnSOD) from the Cu-Zn superoxide dismutase (Cu-Zn SOD).

The MnSOD eluted with 5 mM potassium phosphate pH=7.8 and the Cu-Zn SOD eluted with 50 mM potassium phosphate pH=7.8. The clear solution of Cu-Zn SOD was dialyzed to 50 mM tris pH 7.8, and ammonium sulphate was added to a concentration of 1.6M. This high salt solution of Cu-Zn SOD was then applied to a phenyl-Sepharose column as described in Example 3, step G.

The resulting fractions which eluted in high salt concentration contained highly purified naturally-occurring Cu-Zn superoxide dismutase. The contaminant eucaryotic proteins remained bound to the column until eluted with water.

These results show that the hydrophobic column in the presence of high salt solution binds the majority of liver proteins, and allows the naturally-occurring Cu-Zn superoxide dismutase to pass through, highly purified. Naturally-occurring Cu-Zn superoxide dismutase or analogs thereof may also be purified from other eucaryotic sources such as blood and yeast by this means.

REFERENCES

1. I. Fridovich, Adv. Enzymology 41: 35–97 (1974).
2. J. V. Weisiger, et al., Comp. Biochem. Physiol. 568: 235–238 (1977).
3. J. H. Bloor, et al., Biochem. Genet. 21: 349–364 (1983).
4. H. Tegelstrom, Hereditas 81: 185–198 (1975).
5. L. Civalleri, et al., Mol. Cell. Biochem. 47: 3–9 (1982).
6. S. Marklund, et al., Eur. J. Biochem. 65: 415–422 (1976).
7. C. Beauchamp, et al., Anal. Biochem. 44: 276–278 (1971).
8. B. Lonnerdal, et al., FEBS Lett. 108: 51–58 (1979).
9. I. Fridovich, Adv. Enzymology 58: 61–97 (1986).
10. J. S. Valentine, et al., Metal Ions Biol. 3: 291–358 (1981).
11. Koyama, et al., Transplantation 40(6): 590–595 (1985).
12. Hoo Lim, et al., American College of Surgeons, Surgical Forum Volume XXXVII, 443–445 (1986).
13. Ambrosio, et al., Circulation 75(1): 282–291 (1987).
14. Ambrosio, et al., Circulation 74(6): 1424–1433 (1986).
15. Lieman-Hurwitz, et al., Proc. Natl. Acad. Sci. USA 79: 2808–2811 (1982).
16. Hallewell, et al., Nucleic Acids Res. 13: 2017–2034 (1983).
17. Hallewell, et al., Biotechnology 5: 363–366 (1987).
18. Takahara, et al., Biotechnology 6: 195–198 (1988)

What is claimed is:

1. A method for recovering a solution containing purified, enzymatically active Cu-Zn superoxide dismutase or a polypeptide analog thereof having substantially the same amino acid sequence as, and the biological activity of, naturally-occurring Cu-Zn superoxide dismutase from a composition which comprises cells containing Cu-Zn superoxide dismutase or a polypeptide analog thereof comprising:

(a) treating the composition so as to separate soluble proteins present in the cells from whole cells, cellular debris and insoluble proteins so as to obtain a solution containing such soluble proteins and treating the resulting solution containing the soluble proteins including Cu-Zn superoxide dismutase or polypeptide analog thereof comprising a, b and c isomers of Cu-Zn superoxide dismutase or polypeptide analog thereof, so as to increase the concentration of b isoform and reduce the concentration of a isoform and c isoform of said polypeptide analog contained in the solution;

(b) treating the resulting solution containing the soluble proteins with a second solution containing a salt at a concentration such that the soluble proteins other than Cu-Zn superoxide dismutase or the polypeptide analog thereof present in the solution containing the soluble proteins are rendered capable of binding to an appropriate hydrophobic substance;

(c) contacting the then resulting solution containing the soluble proteins with an appropriate hydrophobic substance so as to bind the soluble proteins other than Cu-Zn superoxide dismutase or the polypeptide analog thereof present in such solution to the hydrophobic substance and thus separate such other proteins from the Cu-Zn superoxide dismutase or polypeptide analog thereof; and (d) recovering the resulting solution containing purified, enzymatically active Cu-Zn superoxide dismutase or polypeptide analog thereof.

2. A method of claim 1, wherein the treatment of the resulting solution prior to step (b) comprises:

(a) treating the resulting solution containing the soluble proteins so as to produce three separate solutions, each of which has an increased concentration of one of either the a, b, or c isoform;

(b) recovering the separate solution which has an increased concentration of the b isoform;

(c) combining the separate solution which has an increased concentration of the a isoform with the separate solution which has an increased concentration of the c isoform;

(d) treating the resulting combined solution so as to produce a solution which has an increased concentration of the b isoform and adding said solution produced to the separate solution recovered in step (b); and (e) recovering the then-resulting solution which has an increased concentration of the b isoform.

3. A method of claim 2, wherein the treatment of the resulting combined solution in step (d) comprises incubation.

4. A method of claim 2, wherein the treatment of the resulting solution in step (a) comprises ion exchange chromatography.

5. A method of claim 2, which further comprises treating the solution with an increased concentration of the b isoform from step (b) or (e) so as to purify the b isoform present in the solution.

6. A method of claim 5, wherein the treatment of the solution comprises ion exchange chromatography.

7. A method of claim 6, wherein the ion exchange chromatography comprises anion exchange chromatography.

8. A method of claim 7, wherein the ion exchange chromatography further comprises cation exchange chromatography.

9. A method of increasing the yield of recovered solutions having an increased concentration of b isoform of an enzymatically-active polypeptide analog of Cu-Zn superoxide dismutase from a composition which comprises cells containing a, b, and c isoforms of the polypeptide analog which comprises:

(a) treating the composition so as to separate soluble proteins present in the cells from whole cells, cellular debris and insoluble proteins so as to obtain a solution containing such soluble proteins, including the a, b and c isoforms;

(b) treating the resulting solution containing the soluble proteins so as to produce three separate solutions, each of which has an increased concentration of one of either of the a, b or c isoforms;

(c) recovering the separate solution which has an increased concentration of the b isoform;

(d) combining the separate solution which has an increased concentration of the a isoform with the separate solution which has an increased concentration of the c isoform;

(e) treating the resulting combined solution so as to produce a solution which has an increased concentration of the b isoform and adding said solution produced to the separate solution recovered in step (c); and (f) recovering the then-resulting solution which has an increased concentration of the b isoform.

10. A method of claim 9, wherein the treatment of the resulting combined solution in step (e) comprises incubation.

11. A method of claim 9, wherein the polypeptide analog of Cu-Zn superoxide dismutase is a polypeptide analog of human Cu-Zn superoxide dismutase.

12. A method of claim 9, wherein the treatment of the composition in step (a) comprises treating the composition so as to disrupt the cells and obtain a cellular extract therefrom, and then subjecting the resulting cellular extract to centrifugation so as to obtain the solution containing the soluble proteins.

13. A method of claim 9, wherein the treatment of the resulting solution containing the soluble proteins so as to produce three separate solutions comprises ion exchange chromatography.

14. A method of claim 9, which further comprises treating the solution with an increased concentration of the b isoform from step (c) or (f) so as to purify the b isoform present in the solution.

15. A method of claim 14, wherein the treatment of the solution comprises ion exchange chromatography.

16. A method of claim 15, wherein the ion exchange chromatography comprises anion exchange chromatography.

17. A method of claim 16, wherein the ion exchange chromatography further comprises cation exchange chromatography.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 37 base pairs (B) TYPE: nucleic acid
        (C) STRANDEDNESS: unknown
        (D) TOPOLOGY: linear (ii) MOLECULE TYPE: protein (iii) HYPOTHETICAL: NO (iv) ANTI-SENSE: NO (v) FRAGMENT TYPE: N-terminal (ix) FEATURE:
        (A) NAME/KEY: CDS
        (B) LOCATION: 23..37

(xi) SEQUENCE DESCRIPTION: SEQ ID NO:1:

AAAAGGAAG AGTATGAGTA TG GCT ACT AAA GCC GTG    37

Ala Thr Lys Ala Val
                    1               5

(2) INFORMATION FOR SEQ ID NO:2:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:2:

Ala Thr Lys Ala Val
1               5